US009839481B2

(12) United States Patent
Blumenkranz et al.

(10) Patent No.: US 9,839,481 B2
(45) Date of Patent: Dec. 12, 2017

(54) HYBRID MANUAL AND ROBOTIC INTERVENTIONAL INSTRUMENTS AND METHODS OF USE

(71) Applicant: Intuitive Surgical Operations, Inc., Sunnyvale, CA (US)

(72) Inventors: Stephen J. Blumenkranz, Redwood City, CA (US); Samuel Kwok Wai Au, Mountain View, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 729 days.

(21) Appl. No.: 14/197,325

(22) Filed: Mar. 5, 2014

(65) Prior Publication Data

US 2014/0257333 A1 Sep. 11, 2014

Related U.S. Application Data

(60) Provisional application No. 61/774,385, filed on Mar. 7, 2013.

(51) Int. Cl.
*A61B 17/28* (2006.01)
*A61B 19/00* (2006.01)
(Continued)

(52) U.S. Cl.
CPC ...... *A61B 19/2203* (2013.01); *A61B 17/2909* (2013.01); *A61B 34/30* (2016.02);
(Continued)

(58) Field of Classification Search
CPC ...... A61B 34/30; A61B 34/71; A61B 19/2203
See application file for complete search history.

(56) References Cited

U.S. PATENT DOCUMENTS 6,331,181 B1 12/2001 Tierney et al.
6,380,732 B1 4/2002 Gilboa
(Continued)

FOREIGN PATENT DOCUMENTS

CN 102469995 A 5/2012
KR 20110003229 A 1/2011
(Continued)

OTHER PUBLICATIONS

Extended European Search Report for Application No. 14760153.8, dated Oct. 20, 2016, 9 pages.
(Continued)

*Primary Examiner* — Aarti B Berdichevsky

(57) ABSTRACT

A system comprises a handpiece body configured to couple to a proximal end of a medical instrument and a manual actuator mounted in the handpiece body. The system further includes a plurality of drive inputs mounted in the handpiece body. The drive inputs are configured for removable engagement with a motorized drive mechanism. A first drive component is operably coupled to the manual actuator and also operably coupled to one of the plurality of drive inputs. The first drive component controls movement of a distal end of the medical instrument in a first direction. A second drive component is operably coupled to the manual actuator and also operably coupled to another one of the plurality of drive inputs. The second drive component controls movement of the distal end of the medical instrument in a second direction.

33 Claims, 21 Drawing Sheets

(51) Int. Cl.
*A61B 17/29* (2006.01)
*A61B 34/00* (2016.01)
A61B 17/00 (2006.01)
A61B 34/30 (2016.01)

(52) U.S. Cl.
CPC .............. *A61B 34/71* (2016.02); *A61B 34/76* (2016.02); *A61B 2017/003* (2013.01); *A61B 2017/00477* (2013.01); *A61B 2017/2923* (2013.01); *A61B 2034/301* (2016.02); *A61B 2034/715* (2016.02)

(56) References Cited

U.S. PATENT DOCUMENTS

| | | | |
|---|---|---|---|
| 6,389,187 B1 | 5/2002 | Greenaway et al. | |
| 6,491,701 B2 | 12/2002 | Tierney et al. | |
| 6,858,005 B2* | 2/2005 | Ohline | A61B 1/0053 600/139 |
| 7,608,083 B2* | 10/2009 | Lee | A61B 17/0469 606/1 |
| 7,772,541 B2 | 8/2010 | Froggatt et al. | |
| 7,781,724 B2 | 8/2010 | Childers et al. | |
| 7,930,065 B2 | 4/2011 | Larkin et al. | |
| 8,257,303 B2* | 9/2012 | Moll | A61B 17/062 600/114 |
| 8,721,530 B2* | 5/2014 | Ohline | A61B 1/0053 600/132 |
| 8,746,533 B2* | 6/2014 | Whitman | A61B 17/07207 227/176.1 |
| 8,888,688 B2* | 11/2014 | Julian | A61B 1/0053 600/132 |
| 8,900,131 B2 | 12/2014 | Chopra et al. | |
| 2003/0045778 A1* | 3/2003 | Ohline | A61B 1/0053 600/114 |
| 2005/0154261 A1* | 7/2005 | Ohline | A61B 1/0053 600/141 |
| 2006/0013523 A1 | 1/2006 | Childers et al. | |
| 2006/0052664 A1* | 3/2006 | Julian | A61B 1/0053 600/146 |
| 2007/0016174 A1* | 1/2007 | Millman | A61M 1/0058 606/1 |
| 2007/0147707 A1* | 6/2007 | Coste-Maniere | G06T 7/0024 382/298 |
| 2008/0255505 A1* | 10/2008 | Carlson | A61B 19/2203 604/95.04 |
| 2009/0036740 A1* | 2/2009 | Finlay | A61B 34/70 600/146 |
| 2009/0171151 A1* | 7/2009 | Choset | A61B 1/00006 600/114 |
| 2010/0076308 A1* | 3/2010 | Wenderow | A61M 25/0113 600/434 |
| 2010/0094088 A1* | 4/2010 | Ohline | A61B 1/0053 600/118 |
| 2010/0185211 A1* | 7/2010 | Herman | B25J 9/1065 606/130 |
| 2011/0306836 A1* | 12/2011 | Ohline | A61B 1/0053 600/146 |
| 2012/0289777 A1 | 11/2012 | Chopra et al. | |
| 2013/0053866 A1* | 2/2013 | Leung | B25J 9/1689 606/130 |
| 2014/0005489 A1* | 1/2014 | Charles | A61B 17/02 600/214 |
| 2015/0133858 A1* | 5/2015 | Julian | A61B 1/00128 604/95.04 |

FOREIGN PATENT DOCUMENTS

| | | |
|---|---|---|
| WO | WO-2004019769 A1 | 3/2004 |
| WO | WO-2010127162 A1 | 11/2010 |
| WO | WO-2012082719 A1 | 6/2012 |

OTHER PUBLICATIONS

Olympus BF Type MP60, Slim Design with a Wide Channel Extends your Reach into the Bronchi, OES Bronchofiberscope, Japan R396SB-3-0604, 2 pages.
Olympus BF Type XP160F, Ultra-Slim Diameter Hybrid, EVIS EXERA Bronchofibervideoscope, Japan R368SB-3-1103.
Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

* cited by examiner

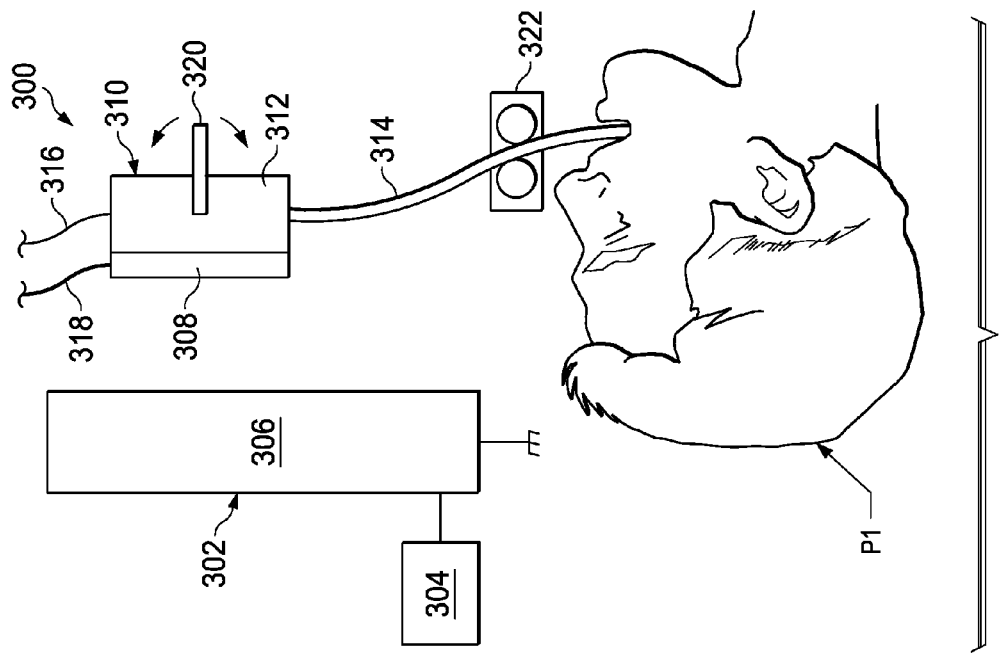
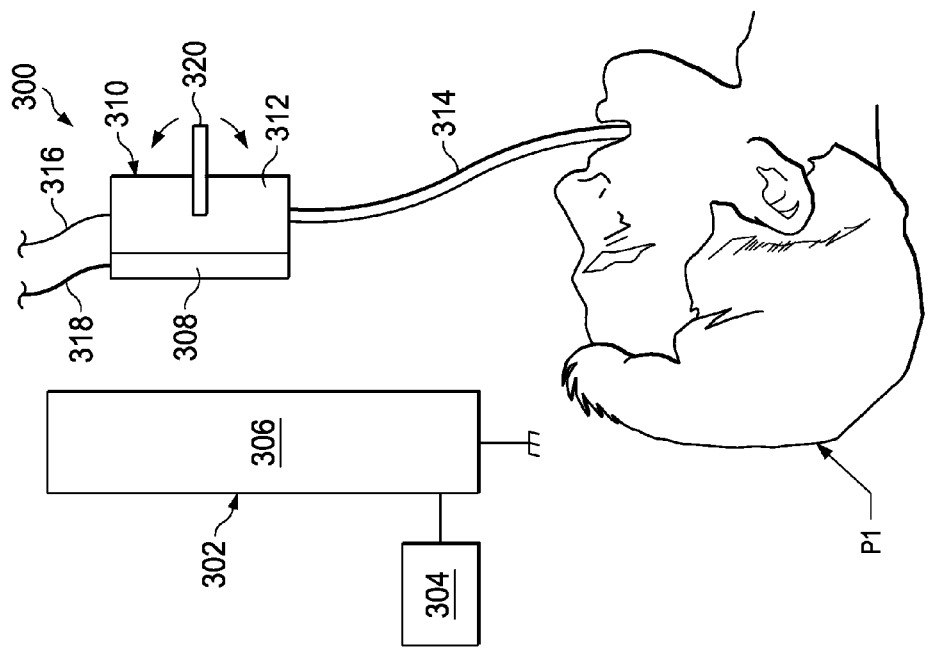

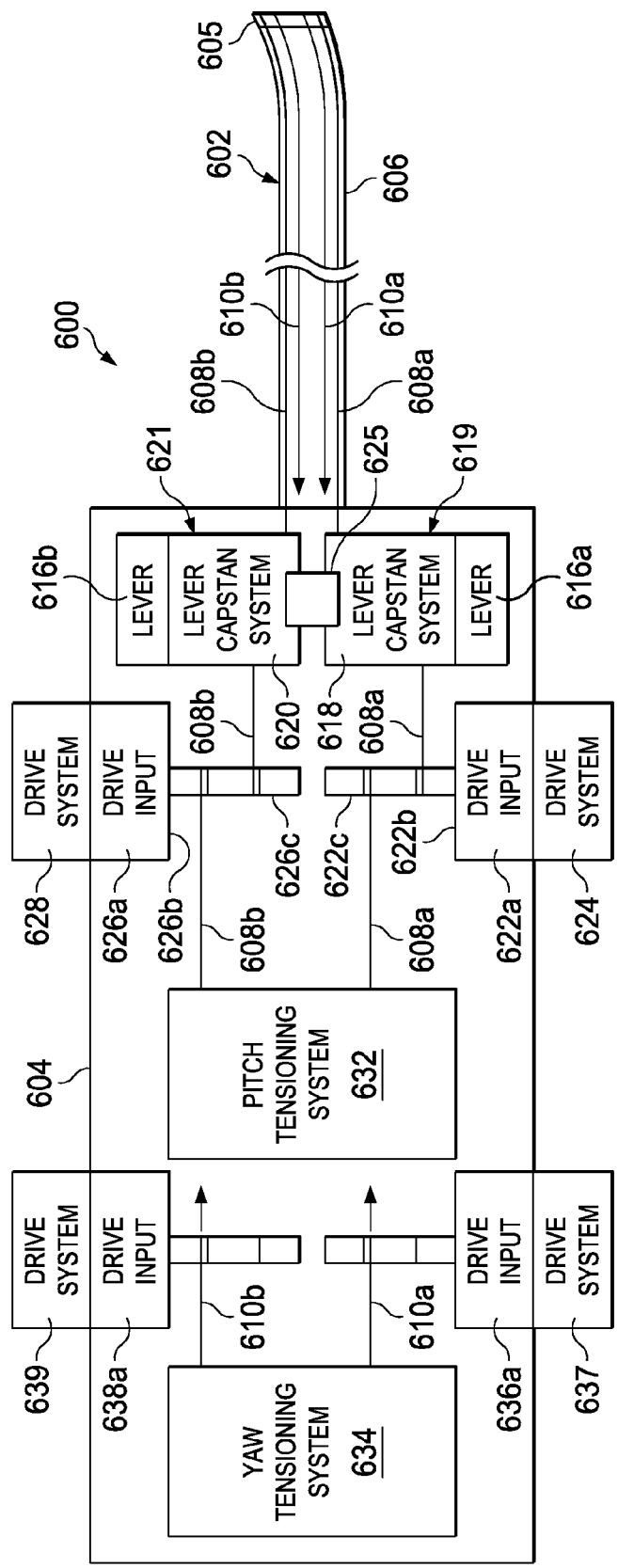

HYBRID MANUAL AND ROBOTIC INTERVENTIONAL INSTRUMENTS AND METHODS OF USE

CROSS-REFERENCE TO RELATED APPLICATIONS

This application claims the benefit of U.S. Provisional Application 61/774,385 filed Mar. 7, 2013, which is incorporated by reference herein in its entirety.

FIELD

The present disclosure is directed to systems and methods for navigating a patient anatomy to conduct a minimally invasive procedure, and more particularly to systems and methods using a hybrid manual and robotic endoscopic instrument to conduct a minimally invasive procedure.

BACKGROUND

Minimally invasive medical techniques are intended to reduce the amount of tissue that is damaged during interventional procedures, thereby reducing patient recovery time, discomfort, and deleterious side effects. Such minimally invasive techniques may be performed through natural orifices in a patient anatomy or through one or more surgical incisions. Through these natural orifices or incisions clinicians may insert interventional instruments (including surgical, diagnostic, therapeutic, or biopsy instruments) to reach a target tissue location. To reach the target tissue location, a minimally invasive interventional instrument may navigate natural or surgically created passageways in anatomical systems such as the lungs, the colon, the intestines, the kidneys, the heart, the circulatory system, or the like. Current interventional instruments are either manually controlled or robotically controlled. In manually controlled systems, a clinician controls the insertion of the interventional instrument and the manipulation of the distal end of the interventional instrument in one or more degrees of freedom. Manually controlled systems rely primarily upon the clinician to navigate a complex network of anatomical passageways to reach a procedure location. Robotically controlled interventional instruments allow a remote user to use advanced imaging and navigation techniques to robotically control the interventional instrument. With robotically controlled systems, the insertion of the instrument and/or movement of the distal end of the surgical instrument in one or more of degrees of freedom may be operated with robotic control. For certain complex interventional procedures, clinicians may prefer a hybrid approach, in which a single interventional instrument may be operated with manual control for a portion of the procedure and with robotic control for other portions of the procedure. Improved systems and methods are needed for providing manual and robotic control to a common interventional instrument.

SUMMARY

The embodiments of the invention are summarized by the claims that follow the description.

In one embodiment, a system comprises a handpiece body configured to couple to a proximal end of a medical instrument and a manual actuator mounted in the handpiece body. The system further includes a plurality of drive inputs mounted in the handpiece body. The drive inputs are configured for removable engagement with a motorized drive mechanism. A first drive component is operably coupled to the manual actuator and operably coupled to one of the plurality of drive inputs. The first drive component controls movement of a distal end of the medical instrument in a first direction. A second drive component is operably coupled to the manual actuator and operably coupled to another one of the plurality of drive inputs. The second drive component controls movement of the distal end of the medical instrument in a second direction.

In another embodiment, a method of operating a medical instrument comprises providing the medical instrument coupled to a handpiece body, a manual actuator mounted in the handpiece body, a plurality of drive inputs mounted in the handpiece body, and first and second drive components extending within the handpiece body. While the plurality of drive inputs are coupled to a motorized drive mechanism, one of the plurality of drive inputs is activated to move at least one of the first and second drive components, thereby moving a distal end of the medical instrument in a first degree of freedom. While the plurality of drive inputs are decoupled from the motorized drive mechanism, a user force is received on the manual actuator to move at least one of the first and second drive components, thereby moving the distal end of the medical instrument in the first degree of freedom.

In another embodiment, a system comprises a handpiece body configured to couple to a proximal end of a medical instrument and a manual actuator mounted in the handpiece body. The system also comprises a motorized drive mechanism mounted in the handpiece body. A first drive component is operably coupled to the manual actuator and operably coupled to the motorized drive mechanism. The first drive component controls movement of a distal end of the medical instrument in a first direction. A second drive component is operably coupled to the manual actuator and operably coupled to the motorized drive mechanism. The second drive component controls movement of the distal end of the medical instrument in a second direction.

A method of operating a medical instrument comprises providing the medical instrument coupled to a handpiece body, a manual actuator mounted in the handpiece body, a motorized drive mechanism mounted in the handpiece body, and first and second drive components extending within the handpiece body. While the motorized drive mechanism is activated, at least one of the first and second drive components is moved, thereby moving the distal end of the medical instrument in a first degree of freedom. While the motorized drive mechanism is deactivated, a user force is received on the manual actuator to move at least one of the first and second drive components, thereby moving the distal end of the medical instrument in the first degree of freedom.

Additional aspects, features, and advantages of the present disclosure will become apparent from the following detailed description.

BRIEF DESCRIPTIONS OF THE DRAWINGS

Aspects of the present disclosure are best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion. In addition, the present disclosure may repeat reference numerals and/or letters in the various examples. This repetition is for the purpose of simplicity and clarity and does not in itself dictate a relationship between the various embodiments and/or configurations discussed.

FIG. 1 schematically illustrates a hybrid manual and robotic interventional instrument system utilizing aspects of the present disclosure.

FIG. 5 illustrates another hybrid manual and robotic interventional instrument system of the present disclosure configured for robotic operation.

FIG. 6 illustrates another hybrid manual and robotic interventional instrument system of the present disclosure configured for robotic operation.

FIG. 9a schematically illustrates a hybrid manual and robotic interventional instrument according to another embodiment of the present disclosure.

Figure 9B:
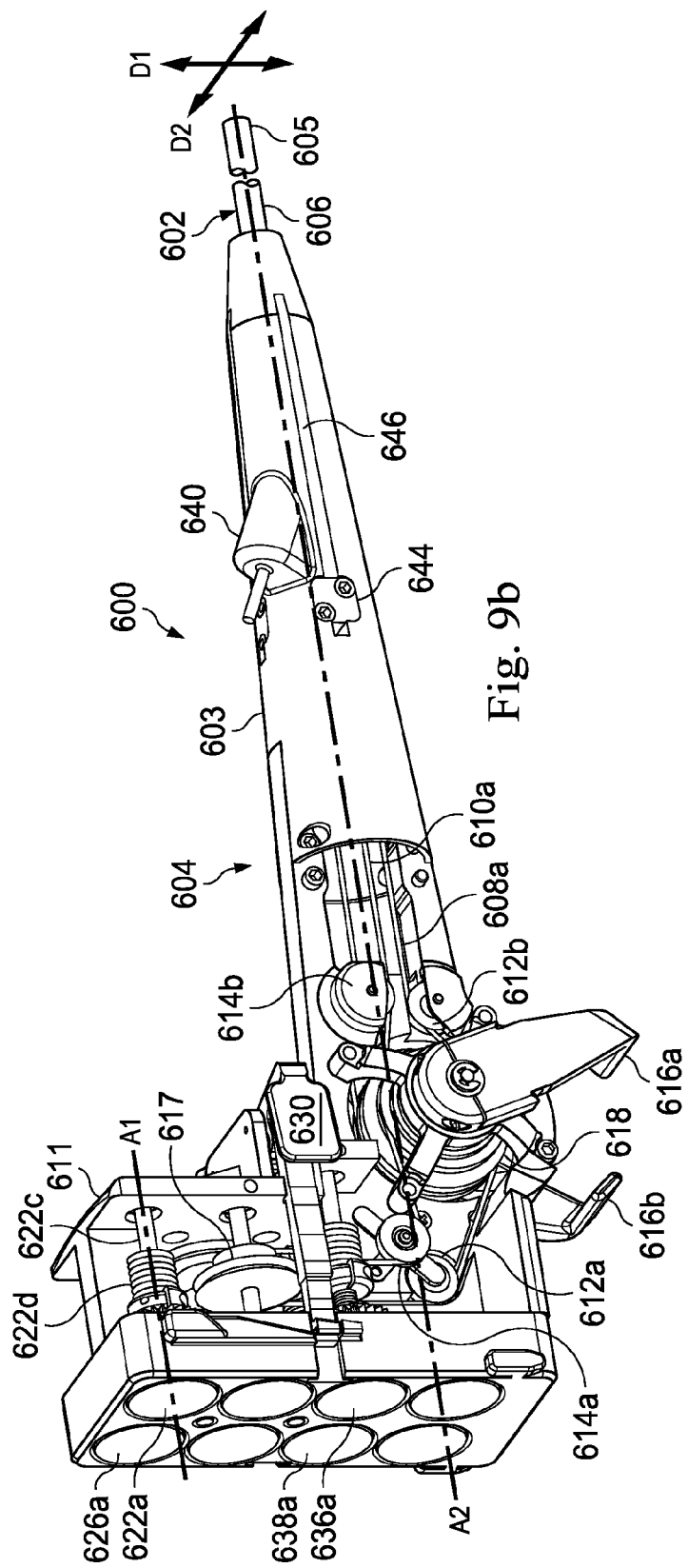

FIGS. 9b, 9c, 9d, 9e, 9f, and 9g illustrate an implementation of the interventional instrument schematically illustrated in FIG. 9a.

Figure 10:
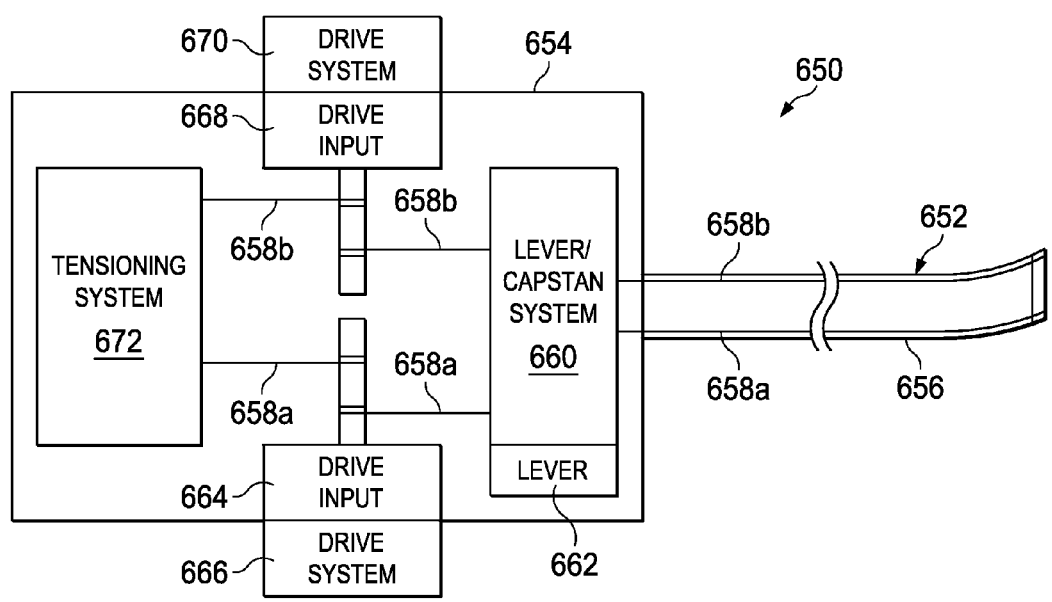

FIG. 10 schematically illustrates a hybrid manual and robotic interventional instrument according to another embodiment of the present disclosure.

Figure 11A:
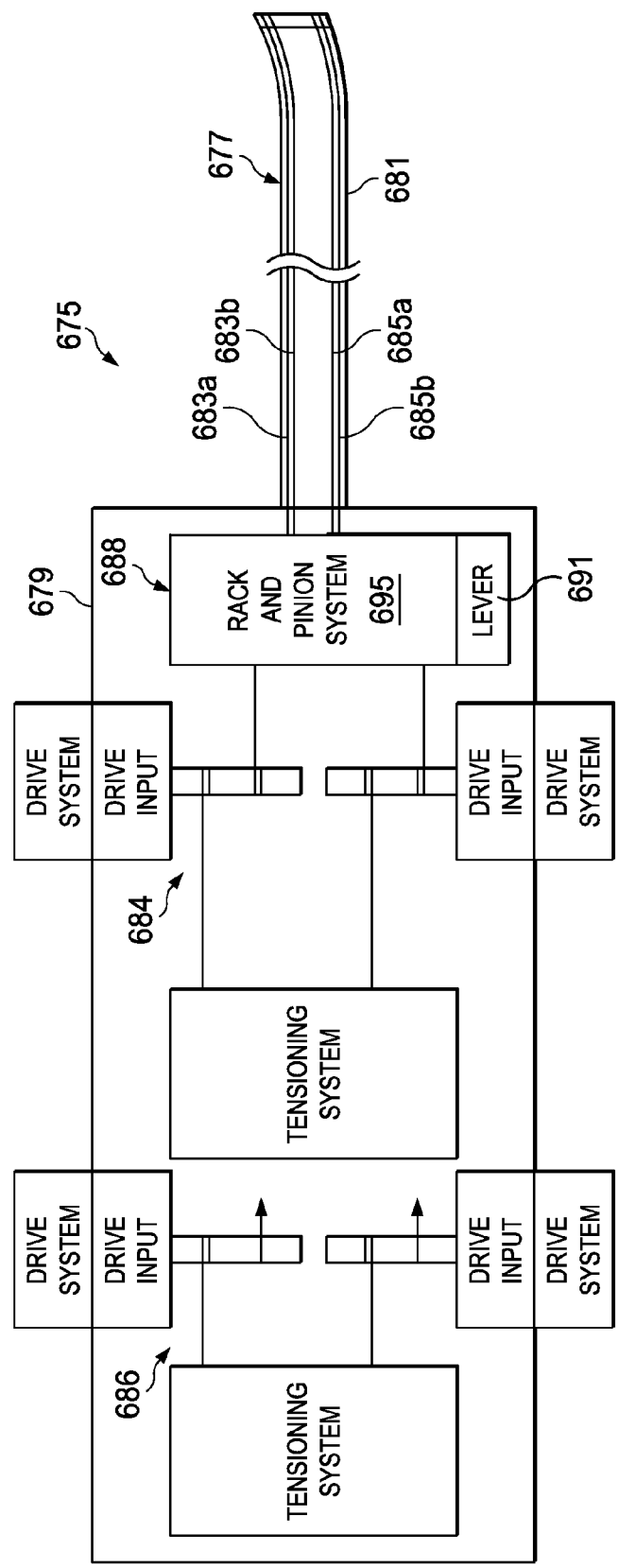

FIG. 11a schematically illustrates a hybrid manual and robotic interventional instrument according to another embodiment of the present disclosure.

Figure 11B:
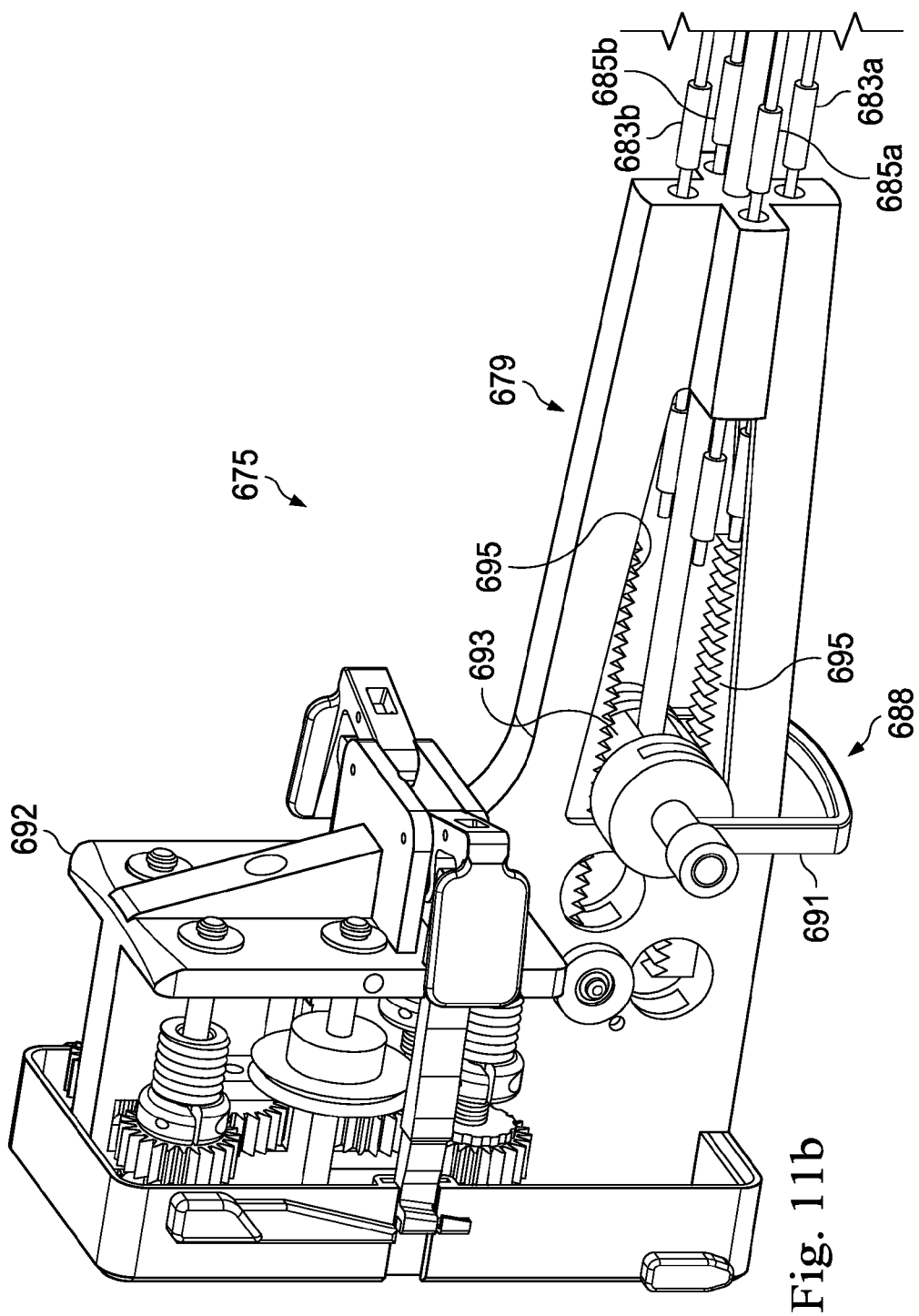

FIG. 11b illustrates an implementation of the hybrid manual and robotic interventional instrument schematically illustrated in FIG. 11a.

Figure 12A:
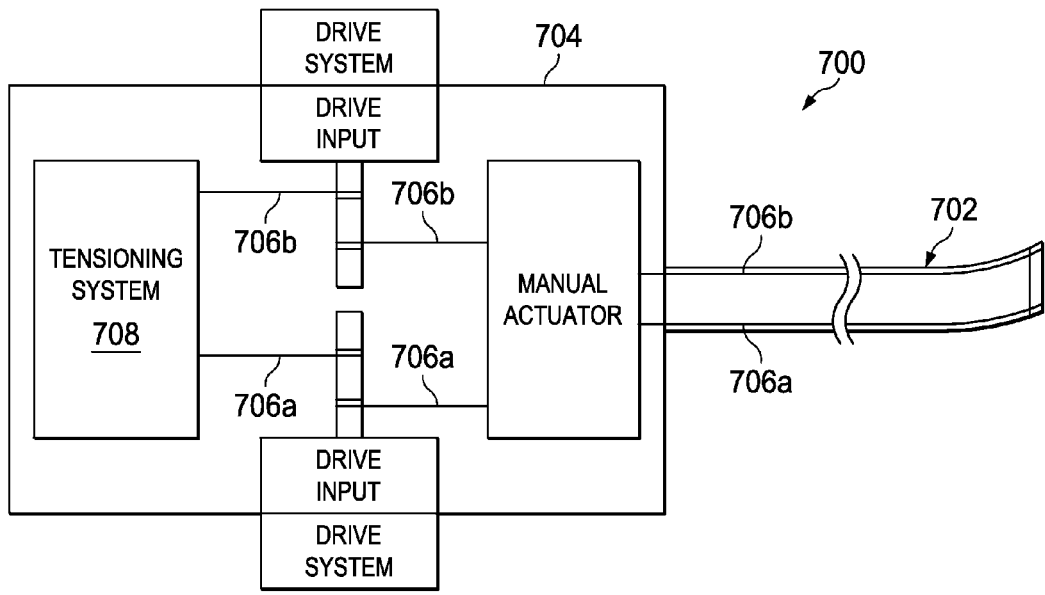

FIG. 12a schematically illustrates a hybrid manual and robotic interventional instrument according to another embodiment of the present disclosure.

Figure 12B:
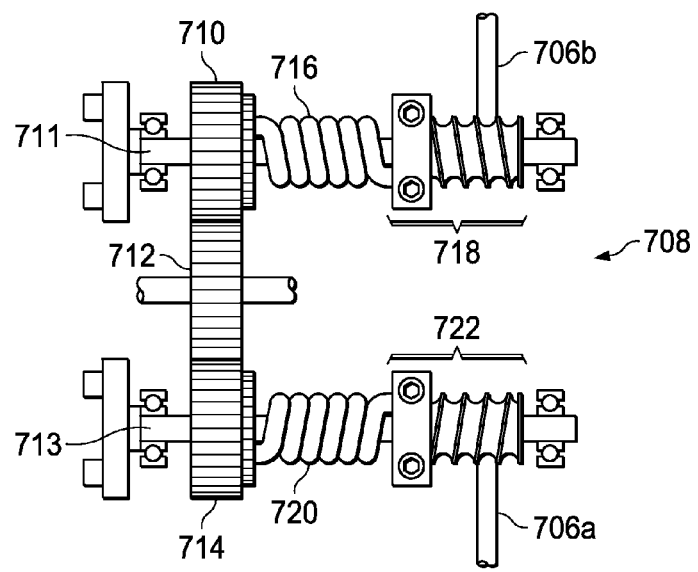

FIG. 12b illustrates an implementation of the tensioning system of the interventional instrument schematically illustrated in FIG. 12a.

Figure 13A:
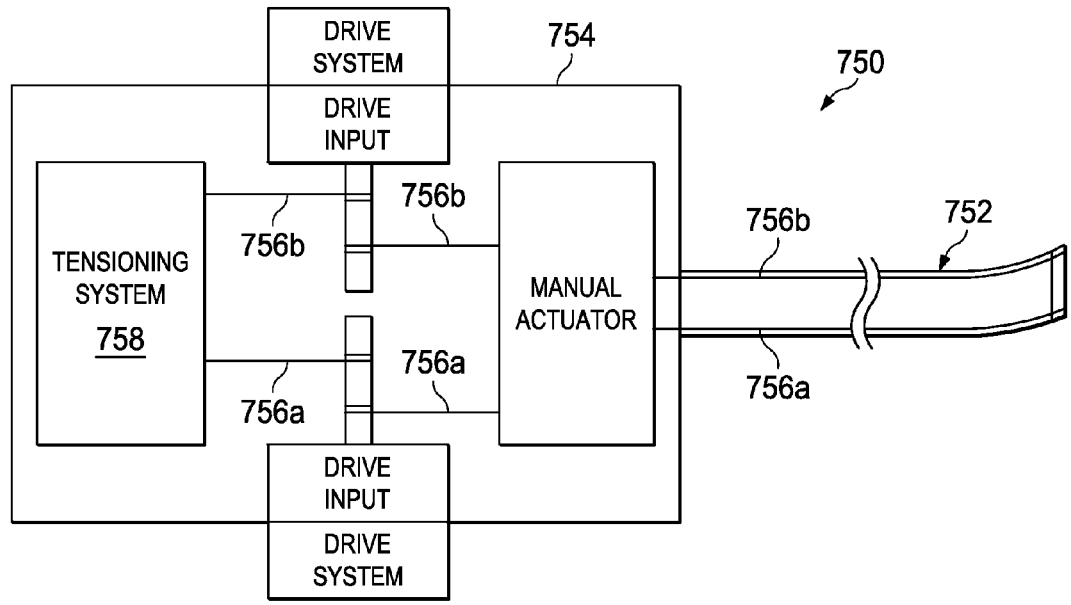

FIG. 13a schematically illustrates a hybrid manual and robotic interventional instrument according to another embodiment of the present disclosure.

Figure 13B:
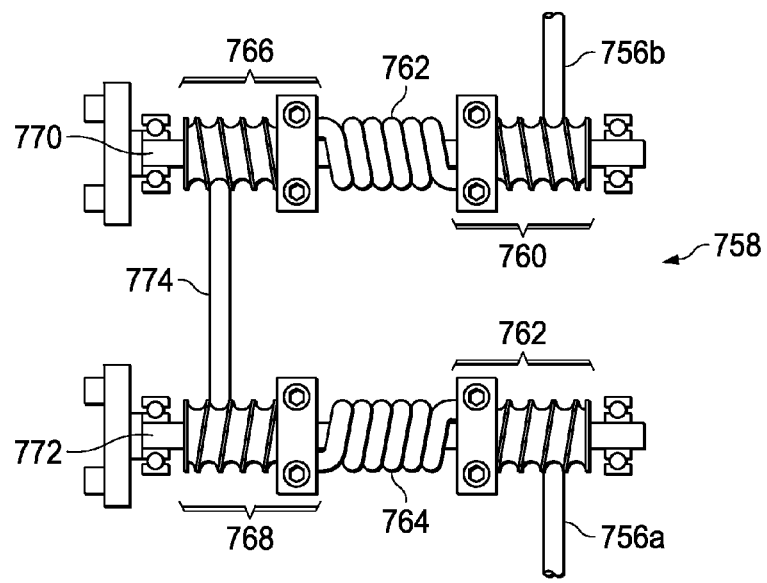

FIG. 13b illustrates an implementation of the tensioning system of the interventional instrument schematically illustrated in FIG. 13a.

Figure 14A:
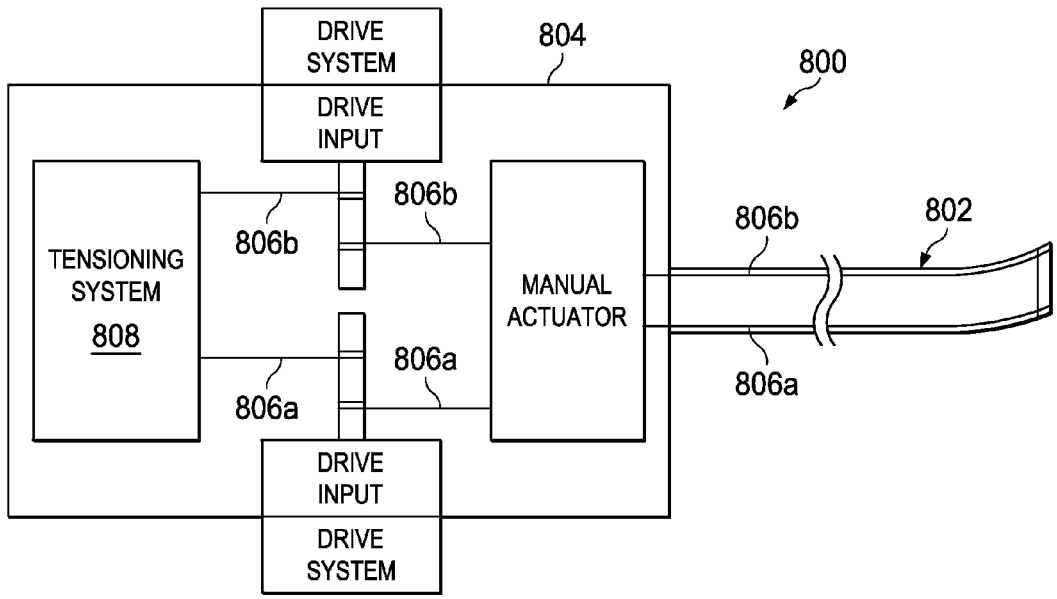

FIG. 14a schematically illustrates a hybrid manual and robotic interventional instrument according to another embodiment of the present disclosure.

Figure 14B:
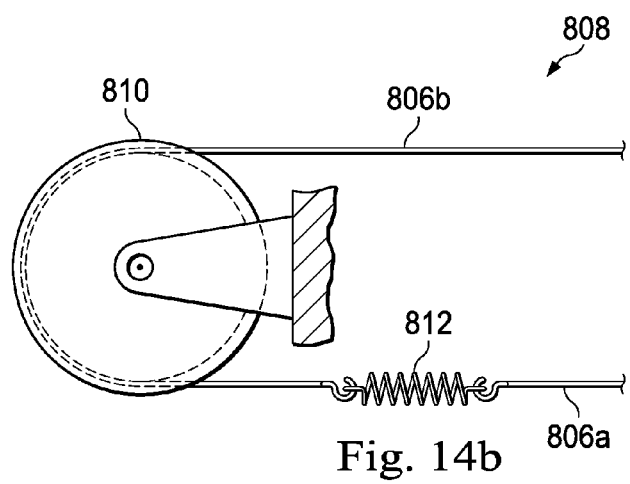

FIG. 14b illustrates an implementation of the tensioning system of the interventional instrument schematically illustrated in FIG. 14a.

Figure 15:
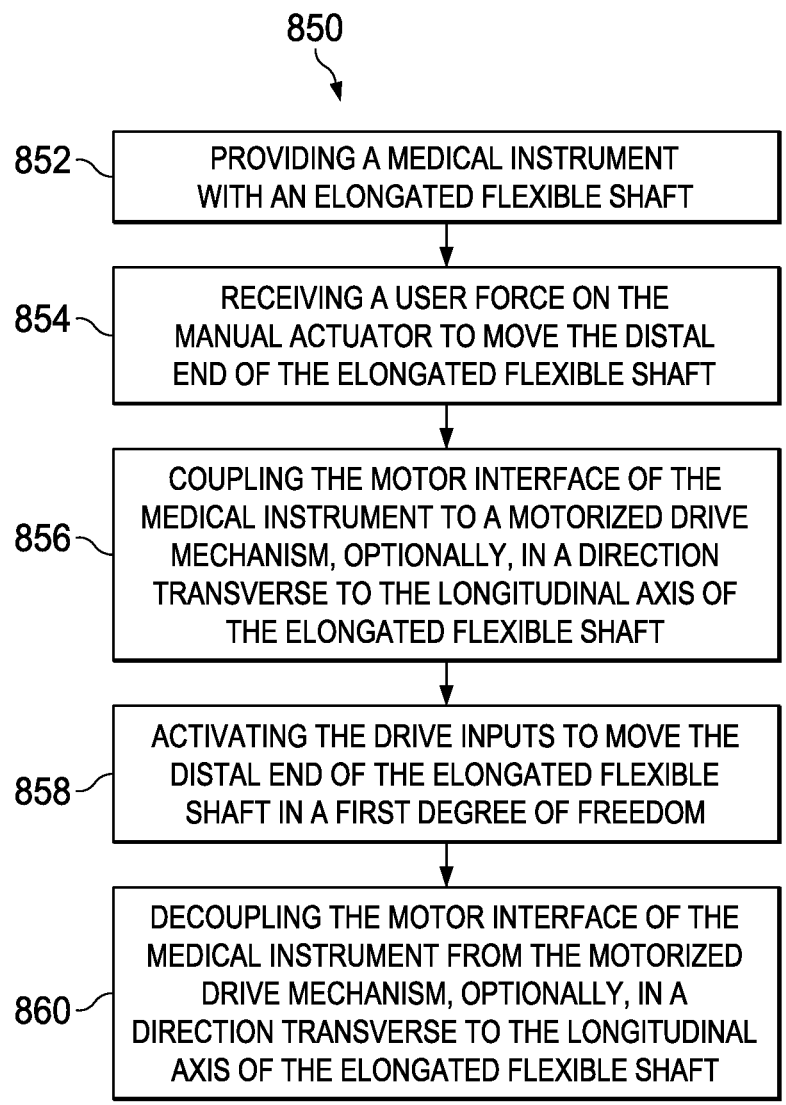

FIG. 15 illustrates a method of use for a hybrid manual and robotic interventional instrument according to an embodiment of the present disclosure.

DETAILED DESCRIPTION

In the following detailed description of the aspects of the invention, numerous specific details are set forth in order to provide a thorough understanding of the disclosed embodiments. However, it will be obvious to one skilled in the art that the embodiments of this disclosure may be practiced without these specific details. In other instances well known methods, procedures, components, and circuits have not been described in detail so as not to unnecessarily obscure aspects of the embodiments of the invention. And, to avoid needless descriptive repetition, one or more components or actions described in accordance with one illustrative embodiment can be used or omitted as applicable from other illustrative embodiments.

The embodiments below will describe various instruments and portions of instruments in terms of their state in three-dimensional space. As used herein, the term "position" refers to the location of an object or a portion of an object in a three-dimensional space (e.g., three degrees of translational freedom along Cartesian X, Y, Z coordinates). As used herein, the term "orientation" refers to the rotational placement of an object or a portion of an object (three degrees of rotational freedom—e.g., roll, pitch, and yaw). As used herein, the term "pose" refers to the position of an object or a portion of an object in at least one degree of translational freedom and to the orientation of that object or portion of the object in at least one degree of rotational freedom (up to six total degrees of freedom). As used herein, the term "shape" refers to a set of poses, positions, or orientations measured along an elongated object.

Figure 1:
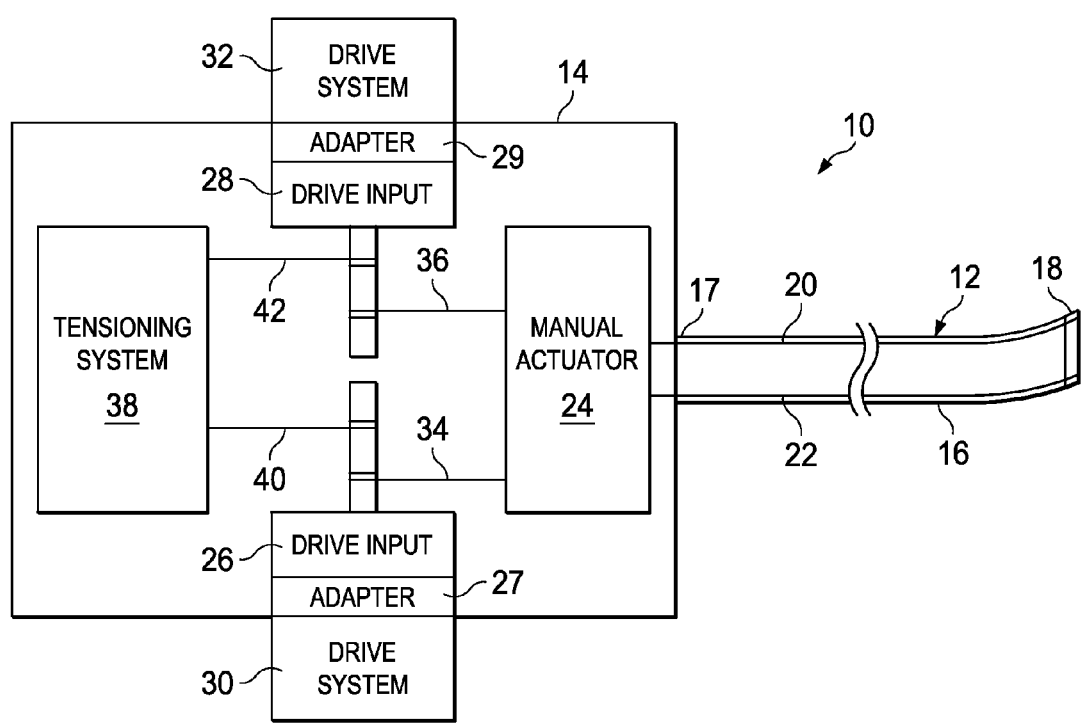

Referring to FIG. 1 of the drawings, a hybrid minimally invasive interventional instrument system 10 utilizes aspects of the present disclosure. The system 10 includes a medical instrument such as a catheter system 12 coupled to an instrument handpiece 14. The catheter system 12 includes an elongated flexible body 16 having a proximal end 17 and a distal end 18. In one embodiment, the flexible body 16 has an approximately 3 mm outer diameter. Other flexible body outer diameters may be larger or smaller. In alternative embodiments, other types of medical instruments may be coupled to and actuated by the instrument handpiece. The flexible body 16 houses opposing drive components 20, 22 for moving the distal end 18 of the flexible body in opposite directions. For example, the drive components may control opposing pitch movements or opposing yaw movements of the distal end 18. In various embodiments, additional sets of opposing drive components may be included to control multiple opposing directions of motion (e.g., pitch, yaw, and roll). The drive components may include tendons, linkages, or other steering controls (not shown) that extend from the instrument handpiece 14 to the distal end 18. Tendons are generally continuous elongated members that can withstand tension. Tendons may include multi-component members such as helical wound or braided cables, ropes, loose fiber rovings, and fiber or wire reinforced belts. Tendons also include single component members such as wires, rods, tubes, bands, filaments or other continuous members suitable for use in tension. The flexible body 16 may further house control mechanisms (not shown) for operating a surgical end effector or another working distal part that is manipulable for a medical function, e.g., for effecting a predetermined treatment of a target tissue. For instance, some end effectors have a single working member such as a scalpel, a blade, a needle, an optical fiber, or an electrode. Other end effectors may include a pair or plurality of working members such as forceps, graspers, scissors, biopsy device, or clip appliers, for example. Examples of electrically activated end effectors include electrosurgical electrodes, transducers, sensors, and the like. Also or alternatively, the flexible body 16 can define one or more lumens through which interventional tools can be deployed and used at a target surgical location. Such interventional tools may include one or more cameras, biopsy devices, laser ablation fibers, medicinal delivery systems, or position and orientation sensors.

The instrument handpiece 14 includes a manual actuator 24 such as a lever or dial movable by a user (e.g., by the user's hand or thumb) to manually control the movement of the opposing drive components 20, 22. The instrument handpiece 14 includes a drive input 26 movable by a drive system 30 to control the movement of the drive component 22 and a drive input 28 movable by a drive system 32 to control the movement of the drive component 20. As will be described in greater detail, below, the drive systems 30, 32 may be motorized components of a robotic interventional system. Optionally, a sterile adaptor disk 27 attached to a sterile drape may be coupled to a drive input (e.g., drive input 26). Similarly, an optional sterile adaptor disk 29 attached to a sterile drape may be coupled to a drive input (e.g., drive input 28). The sterile adaptor disk 27 imparts the motion from the drive system 30 to the drive input 26 while maintaining a sterile barrier between the sterile instrument components and non-sterile robotic components. In alternative embodiments, the optional adaptor disks may be non-sterile, serving to accommodate small mis-alignments between individual motor outputs and instrument inputs. As used herein, removable engagement of drive inputs with drive mechanisms includes direct engagement and indirect engagement via adaptor disks. The drive input 26 may be coupled to the manual actuator 24 by a drive component 34. Drive component 34 may a part of the drive component 22 (i.e., the length of the drive component 22 between the drive input and the manual actuator). Alternatively, drive components 22 and 34 may be separately connected to the manual actuator 24. The drive input 28 may be coupled to the manual actuator 24 by a drive component 36. Drive component 36 may a part of the drive component 20 (i.e., the length of the drive component 20 between the drive input and the manual actuator). Alternatively, drive components 20 and 36 may be separately connected to the manual actuator 24. The instrument handpiece 14 further includes a tensioning system 38 which prevents the opposing drive components 20, 22 from becoming slack and decoupling from the drive inputs or manual actuator. The drive input 26 may be coupled to the tensioning system 38 by a drive component 40. Drive component 40 may a part of the drive component 22 (i.e., the length of the drive component 22 between the drive input and the tensioning system). Alternatively, drive components 40 and 34 may be separately connected to the drive input 26. The drive input 28 may be coupled to the tensioning system 38 by a drive component 42. Drive component 42 may be a part of the drive component 20 (i.e., the length of the drive component 20 between the drive input and the tensioning system). Alternatively, drive components 42 and 36 may be separately connected to the drive input 28.

Figure 2:
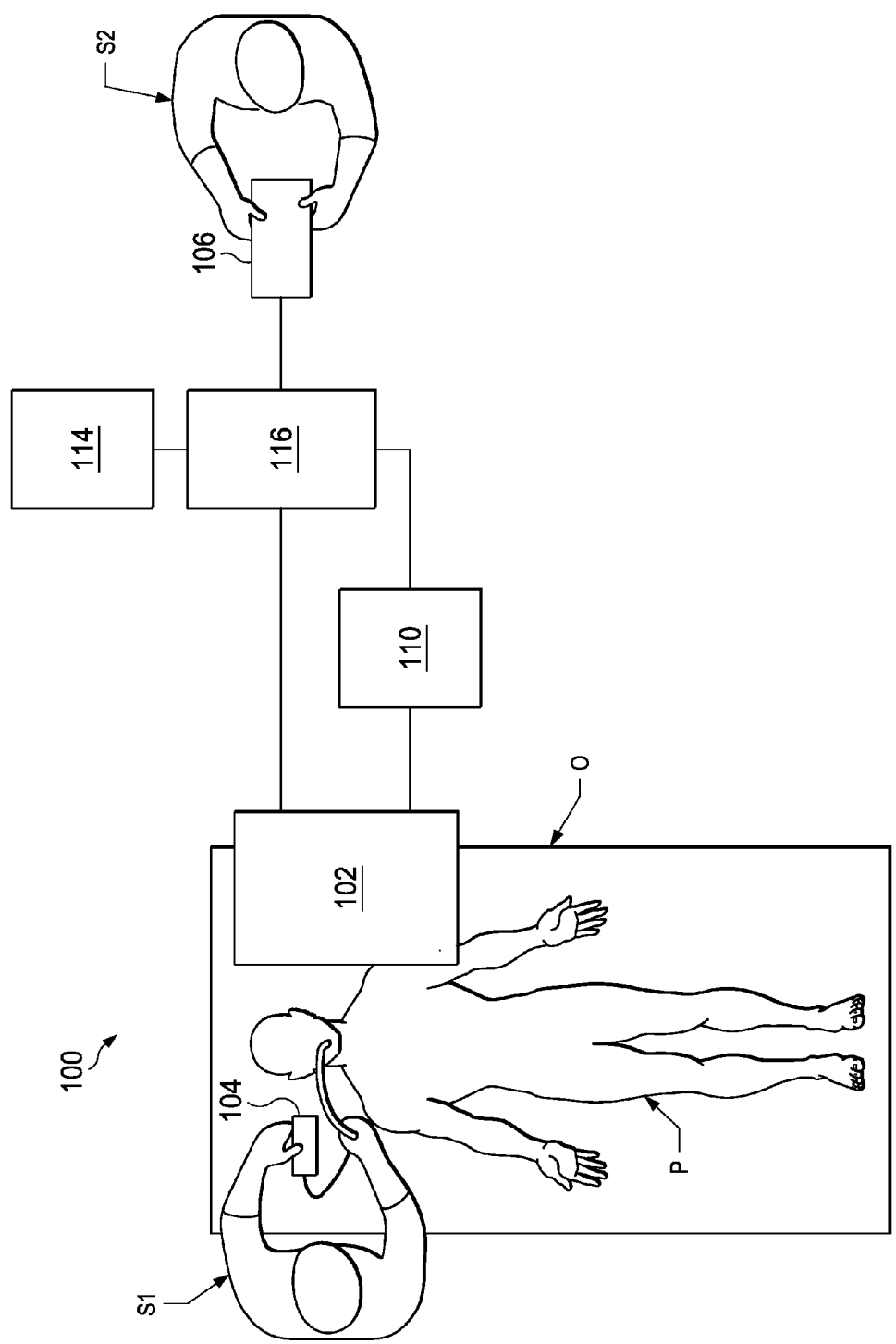
FIG. 2 is a hybrid manual and robotic interventional system, in accordance with embodiments of the present disclosure.

When the hybrid instrument system 10 is used in a robotically controlled mode, the instrument handpiece 14 may be a component of a hybrid manual and robotic interventional system. FIG. 2 illustrates such a system 100. The system 100 may be used for, for example, in surgical, diagnostic, therapeutic, or biopsy procedures. As shown in FIG. 2, the robotic system 100 generally includes an interventional manipulator assembly 102 (e.g., a robotic arm linkage) for operating a hybrid interventional instrument 104 (e.g., the hybrid instrument system 10) in performing various procedures on the patient P. As depicted, the interventional instrument 104 is decoupled from the interventional manipulator 102 for use in manual mode by a surgeon S1. In robotic control mode, the interventional instrument would be coupled to the interventional manipulator 102. (See, e.g. FIG. 3) The manipulator assembly 102 is mounted to or near an operating table O. An operator input system 106 allows a surgeon S2 to view the surgical site and to control the operation of the interventional manipulator assembly 102. In some circumstances, the same person may operate the manual instrument and operate the operator input.

The operator input system 106 may be located at a surgeon's console which is usually located in the same room as operating table O. However, it should be understood that the surgeon S2 can be located in a different room or a completely different building from the patient P. Operator input system 106 generally includes one or more control device(s) for controlling the manipulator assembly 102. The control device(s) may include any number of a variety of input devices, such as hand grips, joysticks, trackballs, data gloves, trigger-guns, hand-operated controllers, voice recognition devices, touch screens, body motion or presence sensors, or the like. In some embodiments, the control device(s) will be provided with the same degrees of freedom as the associated interventional instruments 104 to provide the surgeon with telepresence, or the perception that the control device(s) are integral with the instruments 104 so that the surgeon has a strong sense of directly controlling instruments 104. In other embodiments, the control device (s) may have more or fewer degrees of freedom than the associated interventional instruments 104 and still provide the surgeon with telepresence. In some embodiments, the control device(s) are manual input devices which move with six degrees of freedom, and which may also include an actuatable handle for actuating instruments (for example, for closing grasping jaws, applying an electrical potential to an electrode, delivering a medicinal treatment, or the like).

In alternative embodiments, the robotic system may include more than one manipulator assembly and/or more than one operator input system. The exact number of manipulator assemblies will depend on the surgical procedure and the space constraints within the operating room, among other factors. The operator input systems may be collocated, or they may be positioned in separate locations. Multiple operator input systems allow more than one operator to control one or more manipulator assemblies in various combinations.

An optional sensor system 110 includes one or more sub-systems for receiving information about the instrument 104. Such sub-systems may include a position sensor system (e.g., an electromagnetic (EM) sensor system); a shape sensor system for determining the position, orientation, speed, pose, and/or shape of the catheter tip at (e.g., distal end 18 in FIG. 1) and/or of one or more segments along a flexible body of instrument 104; and/or a visualization system for capturing images from the distal end of the catheter system. The position sensor system, the shape sensor system, and/or the visualization system may interface with a tracking system of the robotic interventional system. The tracking system may be implemented as hardware, firmware, software or a combination thereof which interact with or are otherwise executed by one or more computer processors, which may include the processors of a control system 116, described in greater detail below.

The optional position sensor system may be an EM sensor system that includes one or more conductive coils that may be subjected to an externally generated electromagnetic field. Each coil of the EM sensor system then produces an induced electrical signal having characteristics that depend on the position and orientation of the coil relative to the externally generated electromagnetic field. In one embodiment, the EM sensor system may be configured and positioned to measure six degrees of freedom, e.g., three position coordinates X, Y, Z and three orientation angles indicating pitch, yaw, and roll of a base point. Further description of an EM sensor system is provided in U.S. Pat. No. 6,380,732, filed Aug. 11, 1999, disclosing "Six-Degree of Freedom Tracking System Having a Passive Transponder on the Object Being Tracked," which is incorporated by reference herein in its entirety.

The optional shape sensor system includes an optical fiber aligned with the flexible body of the instrument (e.g., provided within an interior channel (not shown) or mounted externally). In one embodiment, the optical fiber has a diameter of approximately 200 µm. In other embodiments, the dimensions may be larger or smaller.

The optical fiber of the shape sensor system forms a fiber optic bend sensor for determining the shape of the catheter system of instrument 104. In one alternative, optical fibers including Fiber Bragg Gratings (FBGs) are used to provide strain measurements in structures in one or more dimensions. Various systems and methods for monitoring the shape and relative position of an optical fiber in three dimensions are described in U.S. patent application Ser. No. 11/180,389, filed Jul. 13, 2005, disclosing "Fiber optic position and shape sensing device and method relating thereto;" U.S. Provisional Pat. App. No. 60/588,336, filed on Jul. 16, 2004, disclosing "Fiber-optic shape and relative position sensing;" and U.S. Pat. No. 6,389,187, filed on Jun. 17, 1998, disclosing "Optical Fibre Bend Sensor," which are incorporated by reference herein in their entireties. In other alternatives, sensors employing other strain sensing techniques such as Rayleigh scattering, Raman scattering, Brillouin scattering, and Fluorescence scattering may be suitable. In other alternative embodiments, the shape of the catheter may be determined using other techniques.

Optionally, the optical fiber may include multiple cores within a single cladding. Each core may be single-mode with sufficient distance and cladding separating the cores such that the light in each core does not interact significantly with the light carried in other cores. In other embodiments, the number of cores may vary or each core may be contained in a separate optical fiber. In some embodiments, an array of FBG's is provided within each core. Each FBG comprises a series of modulations of the core's refractive index so as to generate a spatial periodicity in the refraction index. The spacing may be chosen so that the partial reflections from each index change add coherently for a narrow band of wavelengths, and therefore reflect only this narrow band of wavelengths while passing through a much broader band. During fabrication of the FBG's, the modulations are spaced by a known distance, thereby causing reflection of a known band of wavelengths. However, when a strain is induced on the fiber core, the spacing of the modulations will change, depending on the amount of strain in the core. Alternatively, backscatter or other optical phenomena that vary with bending of the optical fiber can be used to determine strain within each core. Thus, to measure strain, light is sent down the fiber, and characteristics of the returning light are measured. For example, FBG's produce a reflected wavelength that is a function of the strain on the fiber and its temperature. This FBG technology is commercially available from a variety of sources, such as Smart Fibres Ltd. of Bracknell, England. Use of FBG technology in position sensors for robotic surgery is described in U.S. Pat. No. 7,930,065, filed Jul. 20, 2006, disclosing "Robotic Surgery System Including Position Sensors Using Fiber Bragg Gratings," which is incorporated by reference herein in its entirety.

When applied to a multicore fiber, bending of the optical fiber induces strain on the cores that can be measured by monitoring the wavelength shifts in each core. By having two or more cores disposed off-axis in the fiber, bending of the fiber induces different strains on each of the cores. These strains are a function of the local degree of bending of the fiber. For example, regions of the cores containing FBG's, if located at points where the fiber is bent, can thereby be used to determine the amount of bending at those points. These data, combined with the known spacings of the FBG regions, can be used to reconstruct the shape of the fiber. Such a system has been described by Luna Innovations. Inc. of Blacksburg, Va. The sensing may be limited only to the degrees of freedom that are actuated by the robotic system, or may be applied to both passive (e.g., unactuated bending of the rigid members between joints) and active (e.g., actuated movement of the instrument) degrees of freedom.

The visualization sub-system of sensor system 110 may include an image capture probe extending through the instrument catheter (not shown) for providing concurrent (real-time) image of the surgical site to surgeon. The image capture probe may include a tip portion with a stereoscopic or monoscopic camera disposed near, for example, the distal end 18 of the flexible body 16 of FIG. 1 for capturing images (including video images) that are transmitted to and processed by the robotic interventional system for display. The image capture probe may include a cable coupled to the camera for transmitting the captured image data. Alternatively, the image capture instrument may be a fiber-optic bundle, such as a fiberscope, that couples to the imaging system. The image capture instrument may be single or multi-spectral, for example capturing image data in the visible spectrum, or capturing image data in the visible and infrared or ultraviolet spectrums.

The captured image may be, for example, a two- or three-dimensional image captured by an endoscopic probe positioned within the surgical site. In this embodiment, the visualization sub-system includes endoscopic components that may be integrally or removably coupled to the interventional instrument 104. In alternative embodiments, however, a separate endoscope attached to a separate manipulator assembly may be used to image the surgical site. Alternatively, a separate endoscope assembly may be directly operated by a user, without robotic control. The endoscope assembly may include active steering (e.g., via teleoperated steering wires) or passive steering (e.g., via guide wires or direct user guidance). The visualization system may be implemented as hardware, firmware, software, or a combination thereof, which interacts with or is otherwise executed by one or more computer processors, which may include the processor(s) of a control system 116.

A display system 114 may display an image of the surgical site and interventional instruments generated by sub-systems of the sensor system 110. The display 114 and the operator input system 106 may be oriented such that the relative positions of the imaging device in the scope assembly and the interventional instruments are similar to the relative positions of the surgeon's eyes and hand(s) so the operator can manipulate the interventional instrument 104 and the operator input system 106 as if viewing the workspace in substantially true presence. True presence means that the displayed tissue image appears to an operator as if the operator was physically present at the imager location and directly viewing the tissue from the imager's perspective.

Alternatively or additionally, display system 114 may present images of the surgical site recorded and/or modeled preoperatively using imaging technology such as computerized tomography (CT), magnetic resonance imaging (MRI), fluoroscopy, thermography, ultrasound, optical coherence tomography (OCT), thermal imaging, impedance imaging, laser imaging, nanotube X-ray imaging, or the like. The presented preoperative images may include two-dimensional, three-dimensional, or four-dimensional (including e.g., time based or velocity based information) images and models.

In some embodiments, the display system 114 may display a virtual visualization image in which the actual location of the interventional instrument is registered (e.g., dynamically referenced) with preoperative or concurrent images to present the surgeon with a virtual image of the internal surgical site at the location of the tip of the surgical instrument.

In other embodiments, the display system 114 may display a virtual visualization image in which the actual location of the interventional instrument is registered with prior images (including preoperatively recorded images) or concurrent images to present the surgeon with a virtual image of an interventional instrument at the surgical site. An image of a portion of the interventional instrument may be superimposed on the virtual image to assist the surgeon controlling the interventional instrument.

As shown in FIG. 2, a control system 116 includes at least one processor (not shown), and typically a plurality of processors, for effecting control between the surgical manipulator assembly 102, the operator input system 106, the sensor system 110, and the display system 114. The control system 116 also includes programmed instructions (e.g., a computer-readable medium storing the instructions) to implement some or all of the methods described herein. While control system 116 is shown as a single block in the simplified schematic of FIG. 2, the system may comprise a number of data processing circuits (e.g., on the surgical manipulator assembly 102 and/or on the operator input system 106), with at least a portion of the processing optionally being performed adjacent the surgical manipulator assembly, a portion being performed adjacent the operator input system, and the like. Any of a wide variety of centralized or distributed data processing architectures may be employed. Similarly, the programmed instructions may be implemented as a number of separate programs or subroutines, or they may be integrated into a number of other aspects of the robotic systems described herein. In one embodiment, control system 116 supports wireless communication protocols such as Bluetooth, IrDA, HomeRF, IEEE 802.11, DECT, and Wireless Telemetry.

In some embodiments, control system 116 may include one or more servo controllers to provide force and torque feedback from the interventional instruments 104 to one or more corresponding servomotors for the operator input system 106. The servo controller(s) may also transmit signals instructing manipulator assembly 102 to move instruments which extend into an internal surgical site within the patient body via openings in the body. Any suitable conventional or specialized servo controller may be used. A servo controller may be separate from, or integrated with, manipulator assembly 102. In some embodiments, the servo controller and manipulator assembly are provided as part of a robotic arm cart positioned adjacent to the patient's body.

The control system 116 may further include a virtual visualization system to provide navigation assistance to instrument 104. Virtual navigation using the virtual visualization system is based upon reference to an acquired dataset associated with the three dimensional structure of the anatomical passageways. More specifically, the virtual visualization system processes images of the surgical site recorded and/or modeled using imaging technology such as computerized tomography (CT), magnetic resonance imaging (MRI), fluoroscopy, thermography, ultrasound, optical coherence tomography (OCT), thermal imaging, impedance imaging, laser imaging, nanotube X-ray imaging, or the like. Software is used to convert the recorded images into a two dimensional or three dimensional model of a partial or an entire anatomical organ or anatomical region. The model describes the various locations and shapes of the passageways and their connectivity. The images used to generate the model may be recorded preoperatively or intra-operatively during a clinical procedure. In an alternative embodiment, a virtual visualization system may use standard models (i.e., not patient specific) or hybrids of a standard model and patient specific data. The model and any virtual images generated by the model may represent the static posture of a deformable anatomic region during one or more phases of motion (e.g., during an inspiration/expiration cycle of a lung).

During a virtual navigation procedure, the sensor systems may be used to compute an approximate location of the instrument with respect to the patient anatomy. The location can be used to produce both macro-level tracking images of the patient anatomy and virtual internal images of the patient anatomy. Various systems for using fiber optic sensors to register and display an interventional implement together with preoperatively recorded surgical images, such as those from a virtual visualization system, are known. For example U.S. patent application Ser. No. 13/107,562, filed May 13, 2011, disclosing, "Medical System Providing Dynamic Registration of a Model of an Anatomical Structure for Image-Guided Surgery," which is incorporated by reference herein in its entirety, discloses one such system.

The control system 116 may further include a navigation system for processing information from the virtual visualization system and the sensor tracking system to generate a virtual image display on the display system 114. The system 100 may further include optional operation and support systems (not shown) such as illumination systems, steering control systems, irrigation systems, and/or suction systems.

In robotic control mode, the manipulator assembly 102 supports the hybrid interventional instrument 104 and may comprise a kinematic structure of one or more non-servo controlled links (e.g., one or more links that may be manually positioned and locked in place, generally referred to as a set-up structure) and a robotic manipulator. The robotic manipulator assembly 102 is driven by a plurality of actuators (e.g., motors). These motors actively move the robotic manipulators in response to commands from the control system 116. The motors include drive systems (e.g., drive systems 30, 32) which when coupled to the interventional instrument may advance the interventional instrument into a naturally or surgically created anatomical orifice and/or may move the distal end of the interventional instrument in multiple degrees of freedom, which may include three degrees of linear motion (e.g., linear motion along the X, Y, Z Cartesian axes) and three degrees of rotational motion (e.g., rotation about the X, Y, Z Cartesian axes). Additionally, the motors can be used to actuate an articulable end effector of the instrument for grasping tissue in the jaws of a biopsy device or the like.

In various embodiments, a hybrid interventional instrument system 10, 104 may be a flexible bronchial instrument, such as a bronchoscope or bronchial catheter for use in examination, diagnosis, biopsy, or treatment of a lung. A hybrid manual/robotic instrument may be useful for bronchial procedures because in the manual mode, decoupled from robotic control, a bronchoscopist is able to manually navigate the instrument through the patient's mouth, nose, or a tracheal incision and past delicate anatomical structures such as the vocal cords. When navigating these portions of the patient anatomy (especially at the beginning and ending of a procedure), the bronchoscopist may be able to physically sense the position and orientation of the distal end of the instrument based upon clearly discernible visual and tactile cues. Robotic control and navigation may be a safer or more effective form of control after the distal end of the instrument is positioned in the lung where location and orientation determination based on sensors, camera images, pre-operative modeling, and other indirect indicia becomes more complex. Thus, a single instrument that may be selectively operated by either robotic or by manual control may be an efficient solution.

Figure 3:
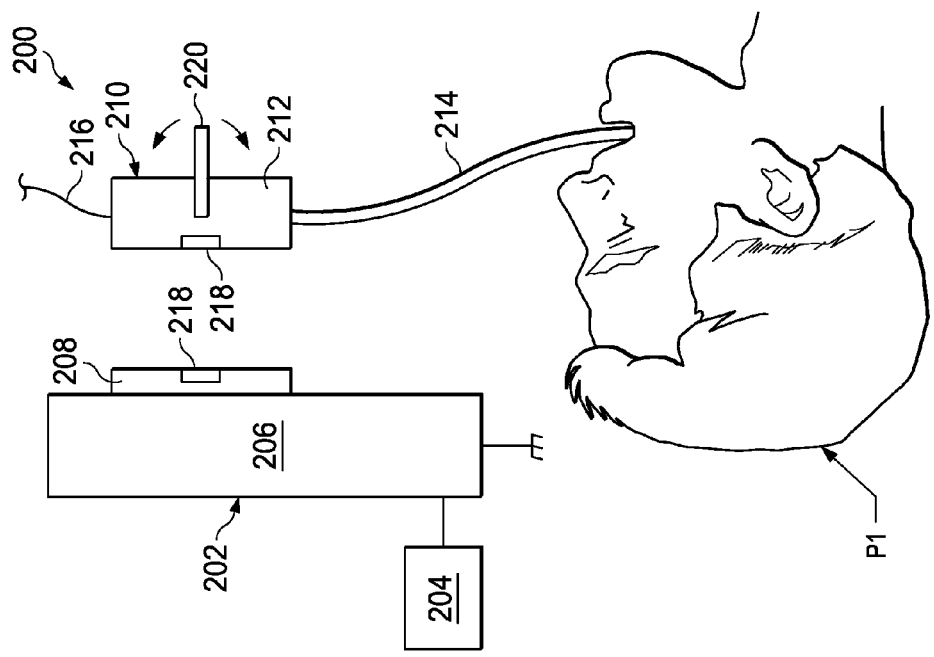
FIG. 3 illustrates a hybrid manual and robotic interventional instrument system of the present disclosure configured for robotic operation.
Figure 4:
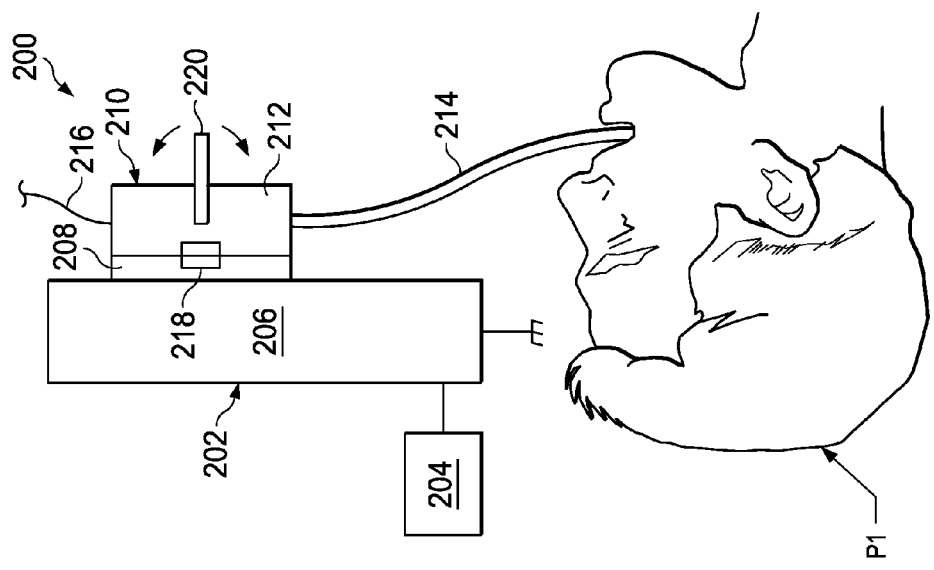
FIG. 4 illustrates the instrument system of FIG. 3 configured for manual operation.

FIGS. 3 and 4 illustrate a robotic interventional system 200 for use in performing a procedure on a patient P1. The robotic interventional system 200 may include any or all of the components of the system 100 but for clarity, only select components are illustrated in FIGS. 3 and 4. The system 200 includes a manipulator assembly 202 (e.g., robotic manipulator assembly 102) controlled by a remote control device 204 (e.g., operator input system 106). The manipulator assembly 202 includes an insertion drive 206 and a pitch and/or yaw drive 208. The drives 206, 208 may be, for example, servo motor drive mechanisms. An interventional instrument 210 includes a handpiece 212 and a flexible body 214 sized for insertion into an anatomic passageway of patient P1. An optical fiber 216 passes through the handpiece 212 and the flexible body 214 for measuring the shape of the flexible body or for recording images from the distal end of the flexible body. A latching mechanism 218 mechanically couples the handpiece 212 to the manipulator assembly 202. The handpiece 212 includes a manual actuator 220.

In the configuration of FIG. 3, the interventional instrument 210 is connected to the manipulator assembly 202 for use in a robotic control mode. The insertion drive 206 controls motion of the flexible body 214 in and out of the patient P1 in response to a user input at the remote control device 204. The drive 208 controls the motion of a distal end of the flexible body 214 in at least one degree of freedom (e.g., pitch, yaw, or roll) in response to user inputs at the remote control device 204. Optionally, the drive 208 may control motion of the distal end of the flexible body 214 in multiple degrees of freedom. Thus, in this robotic control configuration, the insertion and the distal end motion of the interventional instrument is controlled by the remote user via the robotic manipulator assembly.

In the configuration of FIG. 4, the interventional instrument 210 has been disconnected from the manipulator assembly 202 by disengaging the latching mechanism 218 and decoupling the drives of the manipulator assembly 202 from the drive inputs (not shown) of the handpiece. With the instrument 210 disconnected from the assembly 202, the instrument 210 can be held directly by a user, and the user manually advances or withdraws the flexible body 214 to control the insertion of the instrument. The user may control roll of the flexible body 214 by rotating the handpiece (e.g., by twisting the user's wrist). To control the motion of the distal end of the flexible body 214 in one or more degrees of freedom (e.g., pitch or yaw), the user directly toggles the manual actuator 220. Optionally, the actuator 220 may control motion of the distal end of the flexible body 214 in multiple degrees of freedom.

FIG. 5 illustrates another robotic interventional system 300 for use in performing a procedure on a patient P1. The robotic interventional system 300 may include any or all of the components of the system 100 but for clarity, only select components are illustrated in FIG. 5. System 300 includes a manipulator assembly 302 controlled by a remote control device 304. The manipulator assembly 302 includes an insertion drive 306. An interventional instrument 310 includes a handpiece 312 and a flexible body 314 sized for insertion into an anatomic passageway of patient P1. An optical fiber 316 passes through the handpiece 312 and the flexible body 314 for measuring the shape of the flexible body or for recording images from the distal end of the flexible body. The handpiece 312 includes a manual actuator 320. In this embodiment, a drive mechanism 308 includes servo motors for controlling the motion of the distal end of the flexible body 308 in at least one degree of freedom. The drive mechanism 308 and interventional instrument 310 may be attached to the manipulator assembly 302 such that the insertion and distal end motion of the instrument is robotically controlled as in FIG. 3. In this embodiment, however, the drive mechanism 308 and the instrument 310 may be detached from the manipulator. When detached, the distal end motion of the instrument may continue to be controlled by the mechanism 308. The drive mechanism 308 may be coupled to a power source by a power input 318. Other cables or wireless connections (not shown) may provide control instructions to the drive mechanism 308 from a remote controller. Alternatively, the drive mechanism 308 may include batteries or other self-contained portable power supplies to allow untethered use of the instrument 312. In various alternatives, the drive mechanism 308 may be deactivated while still directly attached to the instrument 312 to allow a user to directly toggle the actuator 320 for manually controlling the motion of the distal end of the instrument in at least one degree of freedom.

FIG. 6 illustrates the robotic interventional system 300 further including an optional insertion drive mechanism 322 coupled to the flexible body 314. Like the drive mechanism 308, the insertion-drive mechanism 322, may be portable and may be separately powered and controlled. When the instrument 310 is detached from the manipulator 302, the advancement and withdrawal of the flexible body 314 from the patient P1 may be controlled by the portable insertion drive mechanism 322.

Figure 7A:
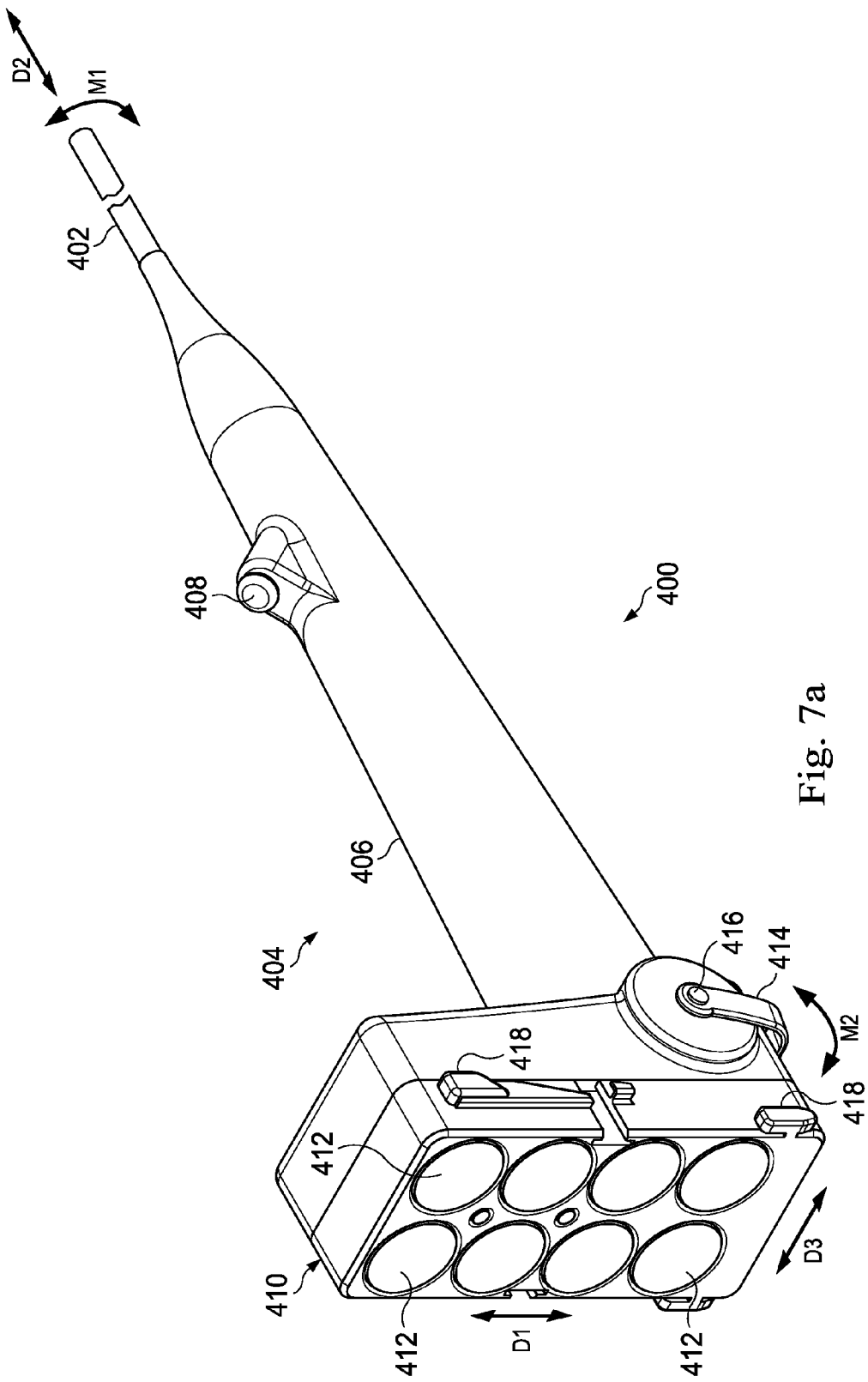
FIGS. 7a & 7b illustrate a hybrid manual and robotic interventional instrument according to an embodiment of the present disclosure.
Figure 7B:
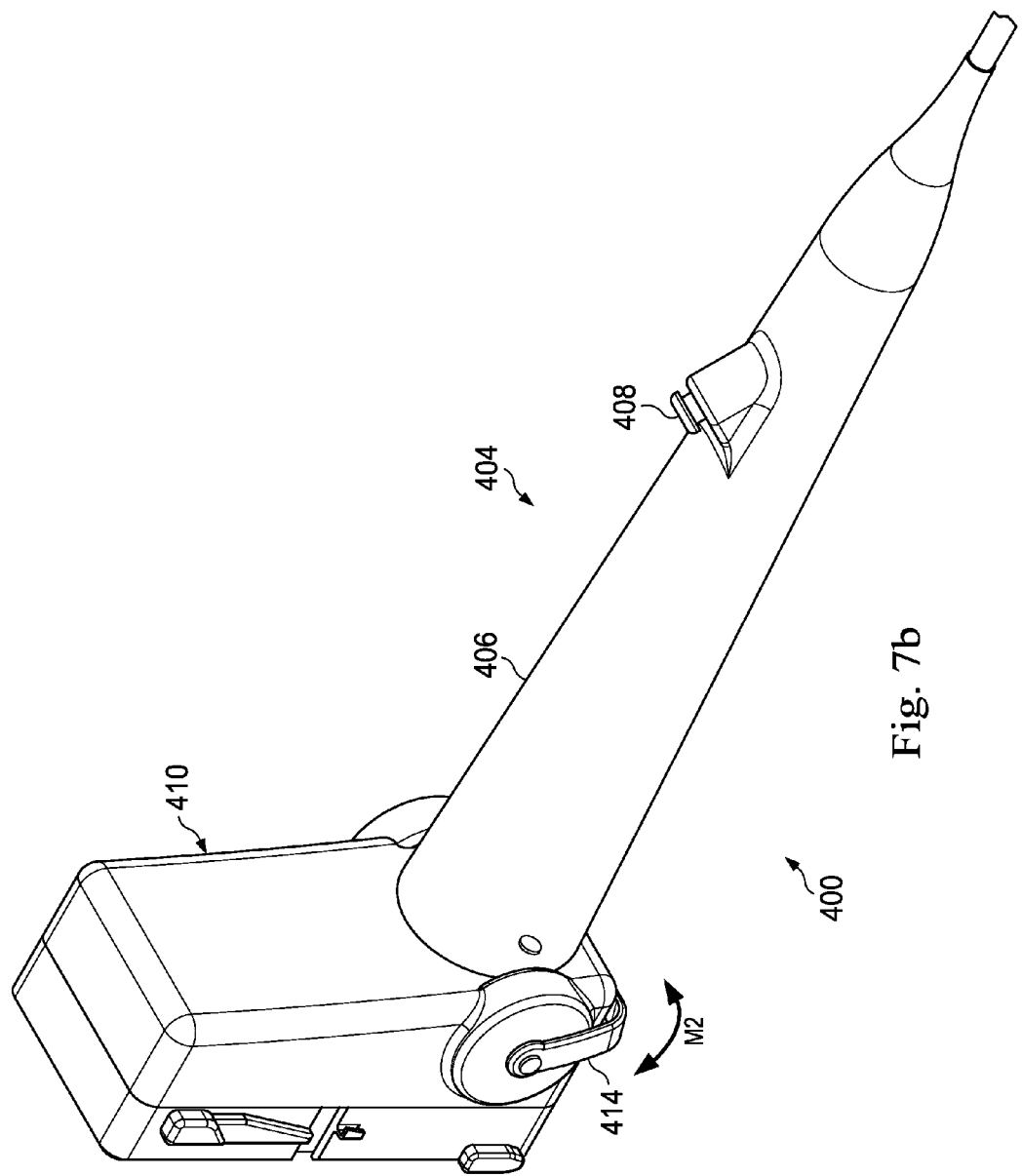

FIGS. 7a & 7b illustrate an interventional instrument 400 according to another embodiment of the present disclosure. The instrument 400 includes an elongated flexible body 402 coupled to a handpiece 404. The handpiece 404 includes a grip portion 406, a tool port 408, and interface housing 410. The handpiece also includes a plurality of drive inputs 412 for interfacing with the drive system of a robotic manipulator. The handpiece 404 further includes a manual actuator 414 pivotable about a pivot 416 for manually controlling the motion of a distal end of the elongated flexible body 402 in at least one degree of freedom (e.g., pitch, yaw, and/or roll). In this and other embodiments, the at least one degree of freedom may be referred to as a pitch motion, but it is understood that one or more manual actuators of the handpiece may control motion of the distal end of the flexible body 402 in one or more other degrees of freedom such as yaw and/or roll.

The tool port 408 is sized and shaped to receive auxiliary tools for insertion through a channel in the flexible body 402. Auxiliary tools may include, for example, cameras, biopsy devices, laser ablation fibers, position and orientation sensors or other surgical, diagnostic, or therapeutic tools. In this embodiment, the grip portion 406 has a tapered shaft sized for comfortable grip by a human hand. In various alternative embodiments, the grip portion may have ergonomic features such as indentions sized to cradle user fingers or non-slip surfaces.

In this embodiment, the handpiece 404 includes engagement features 418, such as elongated protrusions, that cause the handpiece 404 to couple to the robotic manipulator in a direction D1 that is approximately transverse to the insertion direction D2 of the elongated flexible body 402. The transverse coupling direction reduces the risk that coupling the handpiece to the manipulator will move the distal end of the flexible body in the insertion direction D2, thus reducing the risk of injury to the patient or disrupting the navigation that would otherwise result from inadvertent advancement or retraction of the flexible body within the tiny and delicate anatomical passageways of the patient. Alternatively, engagement features may be provided that would cause the handpiece 404 to couple to the robotic manipulator in a direction D3 that is also approximately transverse to the insertion direction D2 of the elongated flexible body 502. The transverse coupling direction would also reduce the risk of moving the handpiece in direction D2 when coupling the handpiece to the robotic manipulator.

In a manual mode, unconnected to a robotic manipulator, a user grasps the grip portion 406 of the instrument 400 and holds the handpiece 404 such that the user's thumb rests near or against the manual actuator 414. The user manually controls insertion motion (i.e., in the direction D2) by advancing or withdrawing the handpiece 404 relative to the patient's anatomy. The user manually controls the pitch motion M1 by pivoting the manual actuator 414 with the motion M2. For example, pivoting the manual actuator toward the distal end of the instrument pitches the distal end of the flexible body up, and pivoting the manual actuator toward the proximal end of the instrument pitches the distal end of the flexible body down. In alternative embodiments, the motion of the manual actuator may cause the pitch motions in the opposite directions. In still other alternatives, the motion of the manual actuator may cause motion of the distal end of the flexible body in other degrees of freedom such as yaw or roll.

In robotic mode, the instrument 400 is directly connected to the robotic manipulator. The drive inputs 412 provide mechanical coupling of the end effector and flexible body steering mechanism with the drive motors mounted to the manipulator. For example, a pair of drive inputs may control the pitch motion M1 of the distal end of the flexible body, with one adaptor of the pair controlling motion in the upward direction and the other of the pair controlling motion in the opposite downward direction. Other pairs of drive inputs may provide opposing motion in other degrees of freedom for the flexible body and/or the end effector. Instrument interfacing with robotic manipulators is described, for example in U.S. Pat. No. 6,331,181, filed Oct. 15, 1999, disclosing "Surgical Robotic Tools, Data Architecture, And Use" and U.S. Pat. No. 6,491,701, filed Jan. 12, 2001 disclosing "Mechanical Actuator Interface System For Robotic Surgical Tools" which are both incorporated by reference herein in their entirety.

Figure 8:
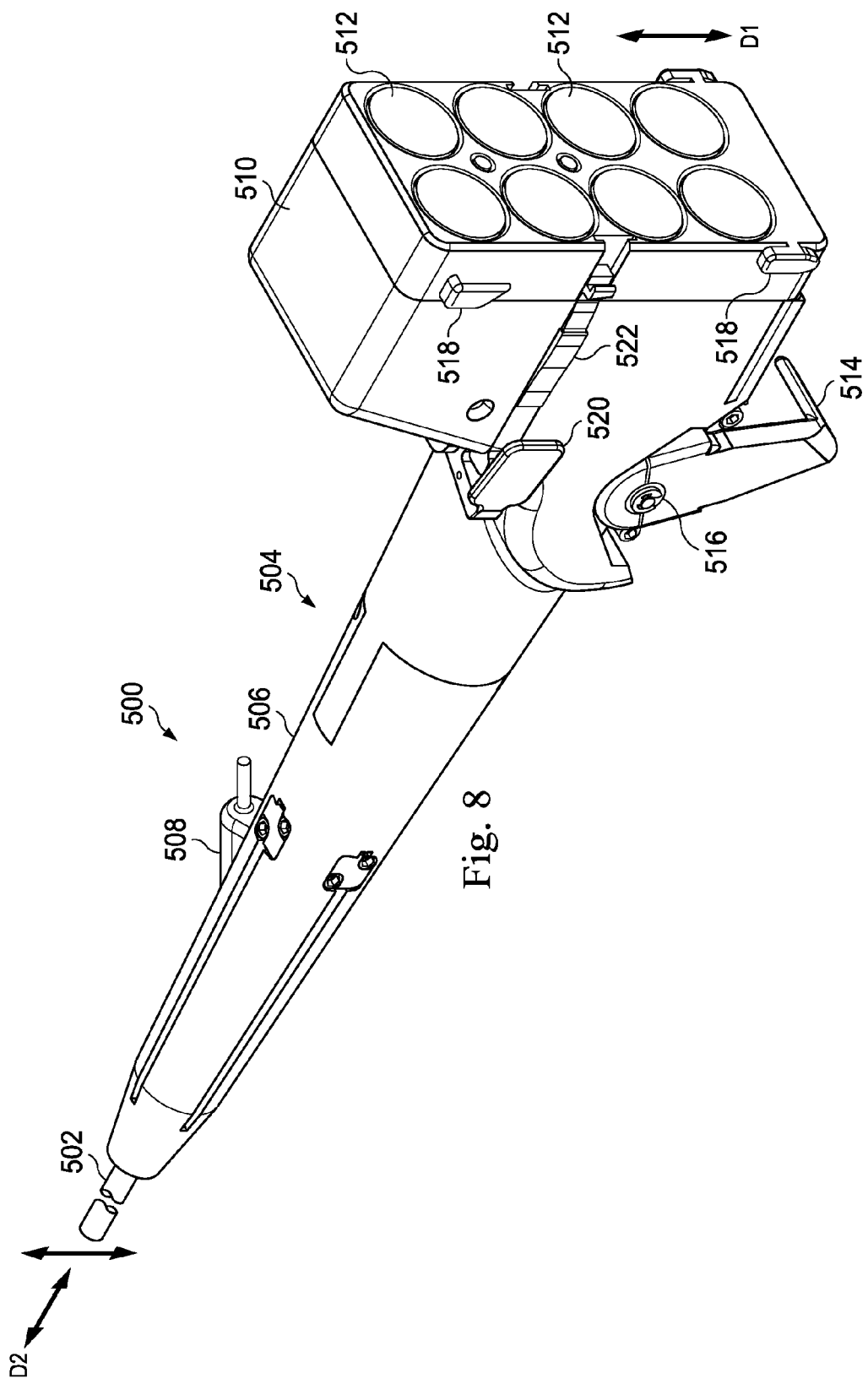
FIG. 8 illustrates a hybrid manual and robotic interventional instrument according to another embodiment of the present disclosure.

FIG. 8 illustrates an interventional instrument 500 according to another embodiment of the present disclosure. The instrument 500 includes an elongated flexible body 502 coupled to a handpiece 504. The handpiece 504 includes a grip portion 506, a tool port 508, and interface housing 510. The handpiece also includes a plurality of drive inputs 512 for interfacing with the drive system of a robotic manipulator.

The handpiece 504 further includes a manual actuator 514 pivotable about a pivot 516 for manually controlling the motion of a distal end of the elongated flexible body 502. In this embodiment, the manual actuator 514 includes two levers (not clearly shown in FIG. 8, but see similar configuration in FIG. 9b). Each of the levers controls opposing motions of a single degree of freedom, e.g., pitch motion. Alternatively, one pivoting lever can control opposing yaw motions and the other pivoting lever can control opposing pitch motions of the distal end of the flexible body.

The tool port 508 is sized and shaped to receive auxiliary tools for insertion through a channel in the flexible body 502. Auxiliary tools may include, for example, cameras, biopsy devices, laser ablation fibers, position and orientation sensors or other surgical, diagnostic, or therapeutic tools. In this embodiment, the grip portion 506 has a tapered shaft sized for comfortable grip by a human hand. In various alternative embodiments, the grip portion may have ergonomic features such as indentions sized to cradle user fingers or non-slip surfaces.

In this embodiment, engagement features, such as elongated protrusions 518, enable the handpiece 504 to couple to the robotic manipulator in the direction D1 that is approximately transverse to the insertion direction D2 of the elongated flexible body 502. The transverse coupling direction reduces the risk that coupling the handpiece manipulator will move the distal end of the flexible body in the insertion direction D2, thus reducing the risk of injury to the patient or disrupting the navigation that would otherwise result from inadvertent advancement or retraction of the flexible body within the tiny and delicate anatomical passageways of the patient.

The handpiece 504 further includes an unlatching mechanism for removing the instrument 500 from the robotic manipulator. In this embodiment, the unlatching mechanism includes a pair of tabs 520 connected by a biasing member (e.g. an extension spring) and connected to a pair of links 522. When the handpiece 504 is coupled to the robotic manipulator, squeezing the tabs 520 together moves the links toward the robotic manipulator, disengaging the handpiece inputs 512 from the robotic manipulator. Then the handpiece 504 may be disengaged from the robotic manipulator, and after disengagement, the instrument 500 may be operated in manual mode. The actuation of the instrument 500 in manual and robotic control modes is similar to the actuation described above for instrument 400 except that the dual lever manual actuator 514 permits a user, in manual mode, to control opposing motions of a single degree of freedom of the distal end of the flexible body (e.g. pitch up and pitch down). Alternatively, a dual lever manual actuator may be configured so that each of the two levers controls a different degree of freedom in two directions (e.g., the right lever controls pitch up and down and the left lever controls yaw left and right).

As shown in FIG. 1, a manual actuator 24 is manipulated by a user to control motion of the distal end of the flexible body when the handpiece 14 is used in manual mode. FIGS. 9a, 10, and 11a illustrate different embodiments for the manual actuator. In other respects, FIGS. 9a, 10a, and 11 are similar to FIG. 1.

FIG. 9a schematically illustrates an interventional instrument 600 and FIGS. 9b, 9c, 9d, 9e, 9f, and 9g illustrate an implementation of the interventional instrument 600 schematically illustrated in FIG. 9a. The system 600 includes a catheter system 602 coupled to an instrument handpiece 604 which includes a grip portion 603. The catheter system 602 includes an elongated flexible body 606. The flexible body 606 houses opposing drive components 608a, 608b for moving the distal end of the flexible body in opposite directions in one degree of freedom (e.g, pitch degree of freedom motion). The flexible body 606 also houses opposing drive components 610a, 610b for moving the distal end of the flexible body in opposite directions in another degree of freedom (e.g. yaw degree of freedom). In this embodiment the drive components are tendons, such as pull wires, that extend from the instrument handpiece 604 to the distal end of the flexible body.

The instrument handpiece 604 includes frame 611 and pulleys 612a, 612b, 613a, 614a, 614b, 615a, 615b rotatably coupled to the frame. Alignment mechanisms 617a, 617b are also coupled to the frame 611. The handpiece 604 further includes a manual actuator 619 that includes a lever 616a mechanically linked to a capstan mechanism 618. The manual actuator 619 also includes a lever 616b mechanically linked to a capstan mechanism 620. A biasing member 625, such as a spring, extends between the capstan mechanisms 618, 620.

The instrument handpiece 604 further includes a drive input 622a movable by a motorized drive system 624 to control the movement of the drive component 608a in one direction of a degree of freedom (e.g., pitch down). The handpiece 604 also includes a drive input 626a movable by a motorized drive system 628 to control the movement of drive component 608b in an opposite direction of the same degree of freedom (e.g., pitch up). The drive systems 624, 628 are components of the robotic manipulator that includes the drive motors. The drive input 622a includes a disk shaped engagement portion 622b and an input shaft portion 622c. A helical groove drive capstan 622d is supported by the shaft portion 622c. The engagement portion 622b may be removably coupled to the drive system 624. The input shaft portion 622c is integrally formed or fixedly coupled to the engagement portion 622b. The drive input 626a includes an engagement portion 622b and an input shaft portion 626c. A helical groove drive capstan 626d is supported by the shaft portion 626c. The engagement portion 626b may be removably coupled to the drive system 628. The input shaft portion 626c is integrally formed or fixedly coupled to the engagement portion 626b. The instrument handpiece 604 further includes a tensioning system 632 (e.g., a pitch tensioning system) which prevents the opposing drive components 608a, 608b from becoming slack and decoupling from or entangling about the drive input capstans, pulleys, or lever capstan mechanisms.

The instrument handpiece 604 further includes a drive input 636a movable by a motorized drive system 637 to control the movement of the drive component 610a in one direction of a degree of freedom (e.g., yaw right). A helical groove drive capstan 636b is connected to the drive input 636a. The handpiece 604 also includes a drive input 638a movable by a motorized drive system 639 to control the movement of drive component 610b in an opposite direction of the same degree of freedom (e.g., yaw left). A helical groove drive capstan 638b is connected to the drive input 638a. The drive systems 637, 639 are components of the robotic manipulator that includes the drive motors. The instrument handpiece 604 further includes a tensioning system 634 (e.g., a yaw tensioning system) which prevents the opposing drive components 610a, 610b from becoming slack and decoupling from the drive inputs capstans or the pulleys. The operation of a gear-based tensioning system such as systems 632, 634 will be described in greater detail for FIGS. 12a, 12b.

In this embodiment, each of the drive components 608a, 608b, 610a, and 610b includes a pull wire portion extending through distal end of the instrument handpiece 604 and into the flexible body 606. The wire portion is coupled, for example by crimping, to a cable portion that extends between the drive input and the wire portion. The cable portion may resist kinks, allowing the drive component to traverse the tight turns in the pulley system of the handpiece. In alternative embodiments, the drive components may be formed from a continuous length of tendon.

A cable portion of the pitch down drive component 608a is wound around the drive capstan 622d and over a portion of the alignment mechanism 617a to align the drive component with the pulley 612a. In this embodiment, the drive component 608a is bent to an angle between approximately 90° and 135° around the pulley 612a. In alternative embodiments, the angles of the cables formed by the pulleys may be larger or smaller. The drive component 608a extends around and is fixed to the lever capstan mechanism 618. Another length of cable of the drive component is fixed to the lever capstan mechanism 618 and extends over the pulley 612b and is crimped to the pull wire portion of the drive component 608a. In alternative embodiments, the cable portion may be continuous without separate portions fixed to the capstan 618.

A cable portion of the pitch up drive component 608b is wound around the drive capstan 626b and over a portion of the alignment mechanism 617b to align the drive component with the pulley 613a. In this embodiment, the drive component 608b is bent to an angle of approximately 90° around the pulley 613a. The drive component extends around and is fixed to the lever capstan mechanism 620. Another length of cable of the drive component is fixed to the lever capstan mechanism 620 and is crimped to the pull wire portion of the drive component 608b. In alternative embodiments, the cable portion may be continuous without separate portions fixed to the capstan 620.

A cable portion of the yaw right drive component 610a is wound around the drive capstan 636b, extends over a pulley 607a and at least partially around the pulley 614b, and is crimped to the pull wire portion of the drive component 610a. A cable portion of the yaw left drive component 610b is wound around the drive capstan 638b, at least partially around the pulley 615a, at least partially around the pulley 607b, and at least partially around the pulley 615b. The cable portion is then crimped to the pull wire portion of the drive component 610b. The various capstans, alignment mechanisms, and pulleys serve to keep the cables untangled, aligned, and free of kinks as the cables traverse the handpiece between the drive inputs and the catheter system. Because the axes of the drive input shafts (e.g., axis A1 of shaft 622c) are generally perpendicular with the axis A2 of the grip portion 603, the drive components may bend at least once at an approximate right angle along their paths within the handpiece 604.

In use in manual mode, a clinician grips the grip portion 603 of the handpiece 604 with a thumb positioned near the levers 616a and 616b. In manual mode, the clinician can control a range of motion (e.g., pitch, roll, and insertion) of the distal end 605 of the catheter 602. To move the distal end 605 of the catheter to pitch downward (D1 down), the clinician pushes the lever 616a (e.g., clockwise in FIG. 9b) which transmits a rotational motion to the lever capstan 618. Rotation of the lever capstan 618 retracts the drive component 608a, causing the distal end 605 of the catheter 602 to pitch downward. The lever 616a may include differently angled surfaces or other tactile cues to allow the clinician to easily recognize the direction of motion associated with each lever. To move the distal end 605 of the catheter to pitch upward (D1 up), the clinician pushes the lever 616b (e.g., clockwise in FIG. 9e) which transmits a rotational motion to the lever capstan 620. Rotation of the lever capstan 620 retracts the drive component 608b, causing the distal end 605 of the catheter 602 to pitch upward. The roll of the distal end 605 of the catheter 602 about axis A2 is controlled by bending of the clinician's wrist. The insertion of the distal end 605 of the catheter 602 is controlled by clinician advancing or retracting the handpiece 604 relative to the patient.

To move the instrument system 600 into robotic control mode, the drive inputs 622a, 626a, 636a, 638a are coupled to motorized drive systems 624, 628, 637, 639, respectively, of a robotic manipulator. As previously described, coupling of the drive inputs and drive systems may occur in a direction transverse to the insertion axis A2 to reduce the risk of advancing or retracting the distal end 605 of the catheter 602.

In robotic control mode, the clinician can control a range of motion (e.g., pitch, yaw, roll, and insertion) of the distal end 605 of the catheter 602. Movement of the drive input 622a turns the capstan 622d and retracts the drive component 608a, causing the distal end 605 of the catheter 602 to pitch downward. Movement of the drive input 626a turns the capstan 626b and retracts the drive component 608b, causing the distal end 605 of the catheter 602 to pitch upward. Movement of the drive input 636a turns the capstan 636b and retracts the drive component 610a, causing the distal end 605 of the catheter 602 to yaw rightward. Movement of the drive input 638a turns the capstan 638b and retracts the drive component 610b, causing the distal end 605 of the catheter 602 to yaw leftward. The roll and insertion of the distal end 605 of the catheter 602 is controlled by movement of the robotic manipulator.

Figure 9C:
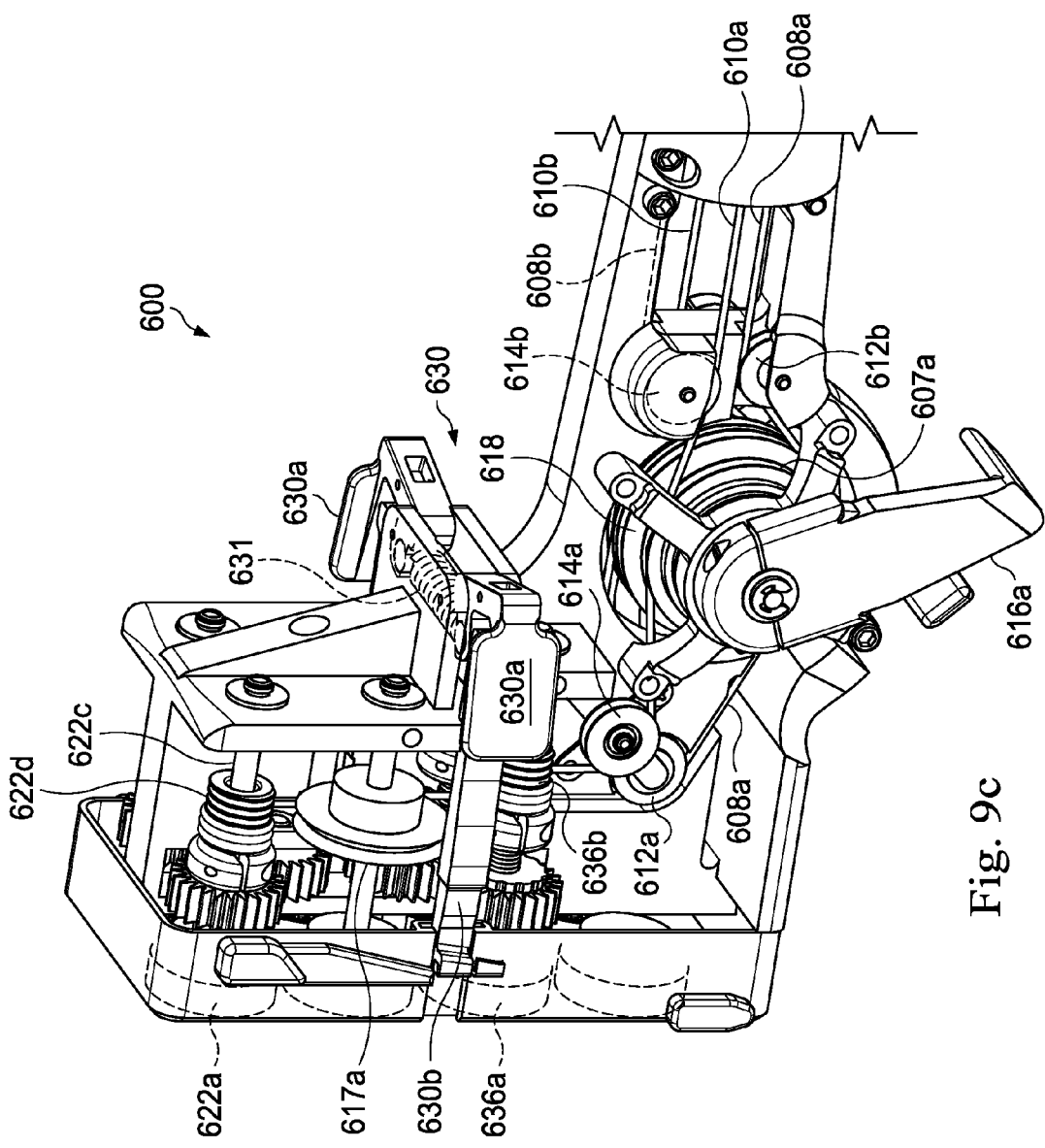
Figure 9D:
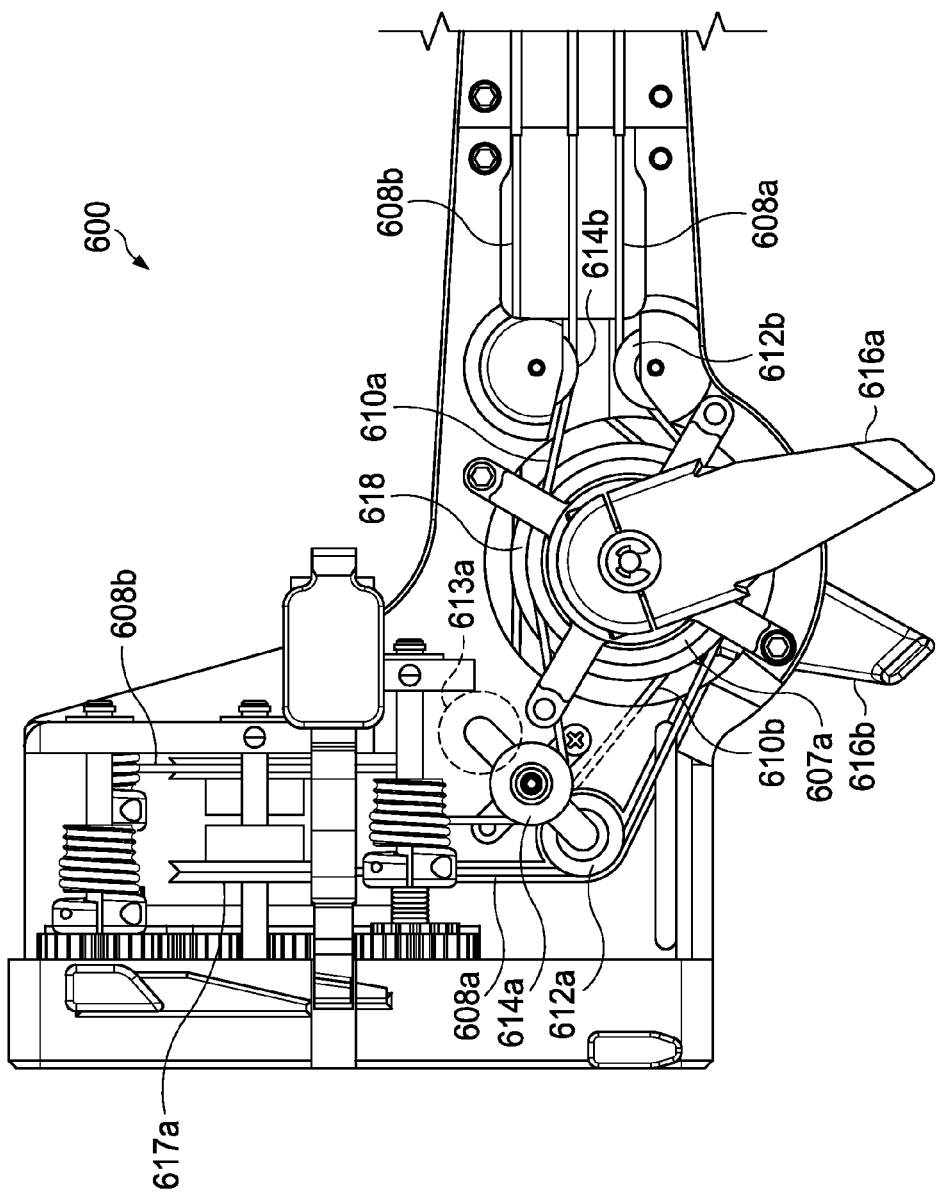
Figure 9E:
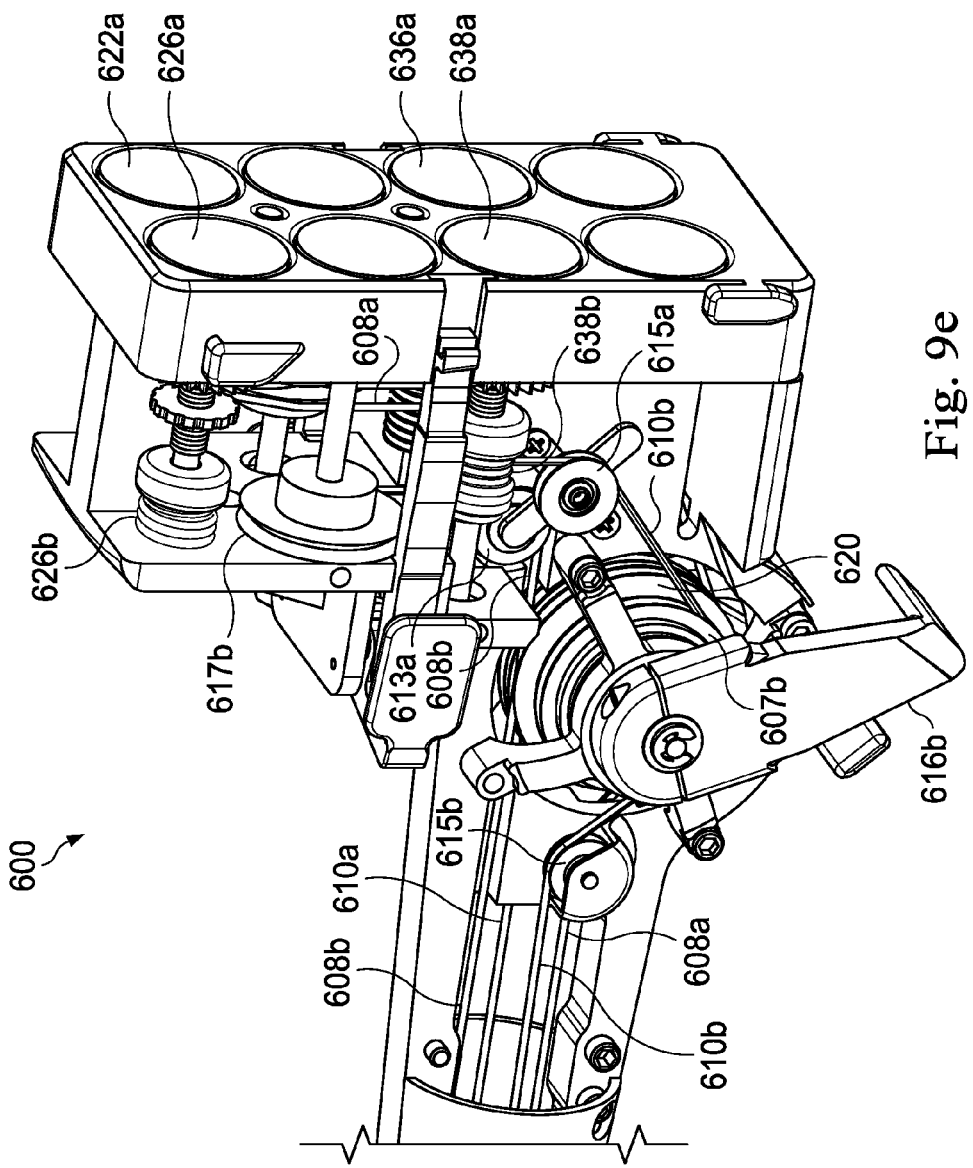
Figure 9F:
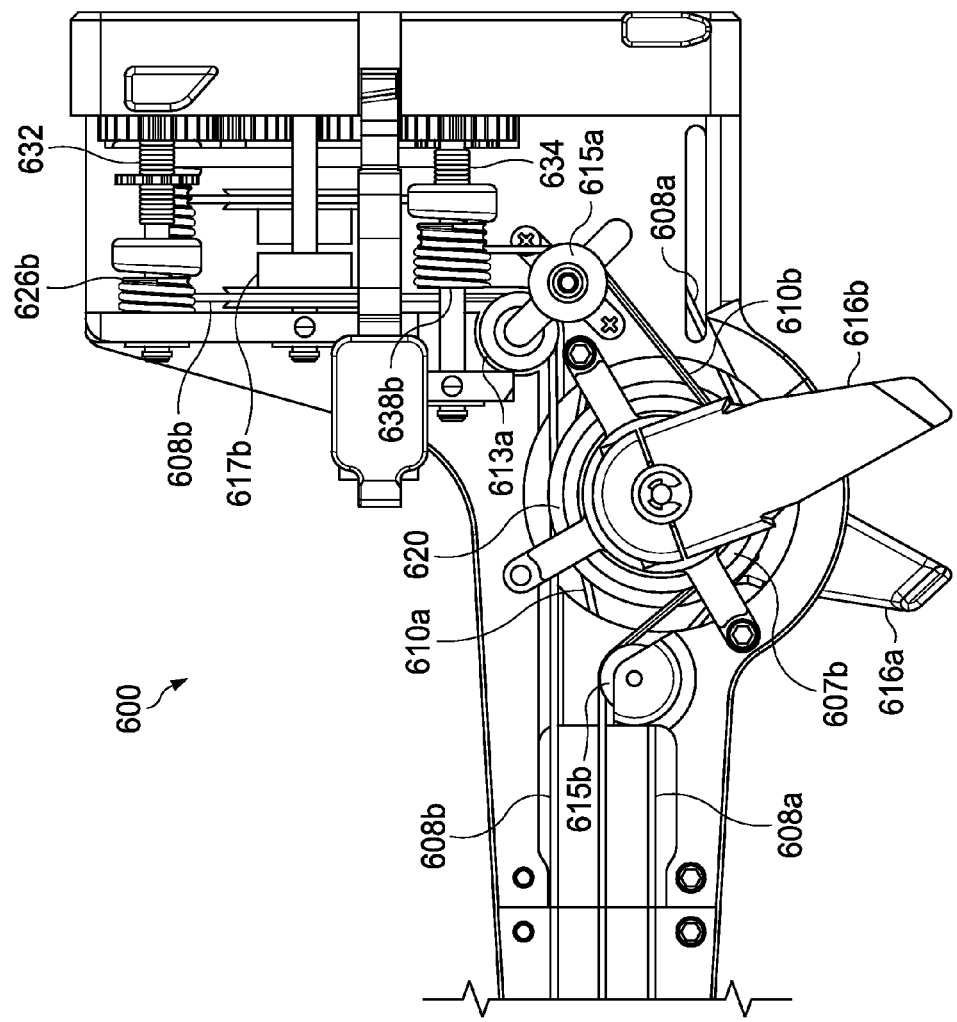

To remove the handpiece 604 from the robotic manipulator and transition the handpiece into manual mode, the tabs 630a of the unlatching mechanism 630 are squeezed, compressing spring 631 (See. FIG. 9c). Squeezing the tabs together moves the links 630b toward the robotic manipulator, optionally moving a plate carrying adaptors such as 27 and 29 of FIG. 1, disengaging the drive inputs from the drive systems and allowing disengagement of hand piece 604 from the robotic manipulator in a direction transverse to axis A2 of body 606.

Figure 9G:
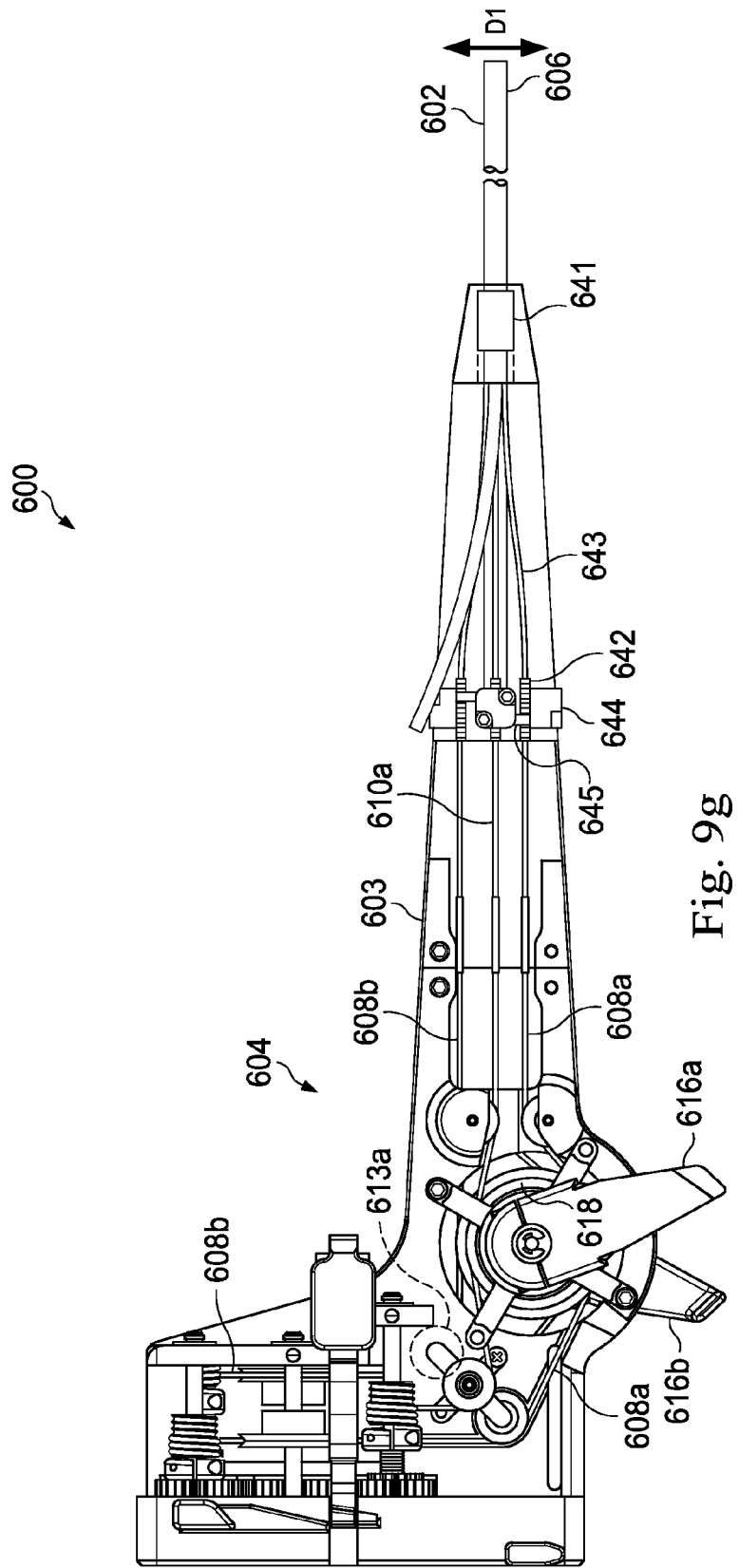

As shown in FIG. 9b, the handpiece 604 also includes a tool port 640 sized and shaped to receive auxiliary tools for insertion through a channel in the flexible body 606. The location of the tool port may be determined to accommodate the drive components and the clinician's grip. Referring to FIG. 9g, the handpiece 604 also includes a collar 641 coupling the flexible body 616 to the grip portion 603. At least a portion of the drive components 608a, 608b, 610a, 610b may be formed of Bowden cable 643 having an elongated inner component (e.g., a wire or cable) movable with respect to and an elongated outer coiled sheath. The inner component may be crimped to the cable portions of the drive components as previously explained. A stud component 642 is attached to the outer coiled sheath (e.g., by epoxy) and is held fixed relative to the grip portion 603 by a clamping plate 644 held in place by fastener 645. As the drive components are manipulated in either manual or robotic control, the Bowden cable portions of the drive components may flex and bulge out through slots 646 (FIG. 9b) in the handpiece 604. This is because with the outer coiled sheath constrained at the proximal end clamping plate is constrained from axial movement along the axis A2.

FIG. 10 schematically illustrates an interventional instrument 650. In this embodiment the interventional instrument has a manual actuator with a single control lever and a tensioning system coupled between opposing drive components. The system 650 includes a catheter system 652 coupled to an instrument handpiece 654. The catheter system 652 includes an elongated flexible body 656. The flexible body 656 houses opposing drive components 658a, 658b for moving the distal end of the flexible body in opposite directions in one degree of freedom (e.g, pitch degree of freedom motion).

The instrument handpiece 654 includes a manual action lever capstan system 660 similar to one of the lever capstan systems 616b/620, 616a/618 of manual actuator 619 disclosed for FIG. 9a. The lever capstan system 660 is coupled to a single lever 662 for manual actuation by a user. Together the lever 662 and lever capstan system 660 form a manual actuator. The instrument handpiece 654 includes a drive input 664 movable by a drive system 666 to control the movement of the drive component 658a. The instrument handpiece 654 also includes a drive input 668 movable by a drive system 670 to control the movement of the opposing drive component 658b. The drive systems 666, 670 are components of the robotic manipulator that includes the drive motors. The instrument handpiece 654 further includes a tensioning system 672 which prevents the opposing drive components 658a, 658b from becoming slack and decoupling from or entangling about the drive inputs or cable wheel system.

In use in manual mode, a clinician operates the single lever 662 to control both opposing motions for a single degree of freedom. For example, advancing the lever may move a distal end of the flexible body to pitch up and retracting the lever may move a distal end of the flexible body to pitch down. In robotic control mode, the instrument system 650 is coupled to a robotic manipulator for control in a manner similar to that described for instrument system 600. In this embodiment, the drive system of the robotic manipulator controls only opposing motions for a single degree of freedom, e.g. pitch up and down. In alternative embodiments, a second drive input set and tensioning system, similar to that disclosed for instrument system 600 may be used to robotically control opposing motions for a second degree of freedom, e.g. yaw right and left.

FIG. 11a schematically illustrates such a second degree of freedom drive input set and tensioning system in an interventional instrument 675 and FIG. 11b illustrates an implementation of the interventional instrument schematically illustrated in FIG. 11a. The system 675 includes a catheter system 677 coupled to an instrument handpiece 679. The catheter system 12 includes an elongated flexible body 681. The flexible body 681 houses opposing drive components 683a, 683b for moving the distal end of the flexible body in opposite directions of a single degree of motion (e.g., pitch). The flexible body 681 also houses opposing drive components 685a, 685b for moving the distal end of the flexible body in opposite directions of another single degree of motion (e.g., yaw). The handpiece 679 includes a pitch control system 684 including drive inputs and a pitch tensioning system similar to that described for handpiece 600. The handpiece 679 also includes a yaw control system 686 including drive inputs and a yaw tensioning system similar to that described for handpiece 600. In this embodiment, a manual actuator 688 includes a single lever 691 mechanically linked to a pinion gear 693 that is mechanically engaged with gear racks 695. The opposing pitch drive components 683a, 683b are coupled to the gear racks 695.

In robotic control mode, the instrument system 675 may be operated substantially as described for instrument system 600. In manual control mode, a clinician operates the lever 691, for example with a thumb, to move the opposing pitch drive components 683a, 683b. In this embodiment, pivoting the lever 691 toward the distal end of the handpiece 679 rotates the gear 693, causing the rack and pinion arms to move in opposite directions, thereby retracting the drive component 683b and advancing the drive component 683a. When the lever 691 is pivoted toward the proximal end of the handpiece 679, the gear 693 rotates, causing the rack and pinion arms to move in opposite directions, thereby retracting the drive component 683a and advancing the drive component 683b.

In various embodiments, drive inputs in the handpiece may be coupled to the motorized drive system of the robotic interventional system so that in robotic control mode the drive inputs control multiple degrees of freedom (e.g., pitch and yaw) while in manual mode fewer degrees of freedom may be controlled by the manual actuator (e.g. pitch only). Alternatively, the same number of degrees of freedom can be controlled in both manual and robotic control.

FIG. 12a schematically illustrates an interventional instrument 700. The instrument 700 includes a catheter system 702 coupled to an instrument handpiece 704. The catheter system 702 houses opposing drive components 706a, 706b for moving the distal end of the flexible body in opposite directions in one degree of freedom (e.g., pitch degree of freedom motion). The instrument 700 has a gear and spring tensioning system 708 which prevents the opposing drive components 706a, 706b from becoming slack and decoupling from or entangling about the drive inputs or manual actuator. Similar tensioning systems 632, 634 are used in instrument system 600.

FIG. 12b illustrates a portion of the tensioning system 708 which includes a gear 710 coupled to a gear 714 by an idling gear 712. The tensioning system 708 may be applied as the tensioning system in any of the instrument systems previously described. Gear 710 is rotatably coupled to a shaft 711 which is rotatably attached to the handpiece 704. A biasing member 716, such as a torsion spring, is coupled at one end to the gear 710 and at another end to a capstan 718 which is fixed to shaft 711. The drive component 706b wraps around the capstan 718. Similarly, gear 714 is rotatably coupled to a shaft 713 which is rotatably attached to handpiece 704. A biasing member 720, such as a torsion spring, is coupled at one end to the gear 714 and at another end to a capstan 722 which is fixed to shaft 713. The drive component 706a wraps around the capstan 722.

Capstan 718 is therefore compliantly coupled to capstan 722 through the gears 710, 712, 714 and the springs 716, 720. Further, drive component 706b is compliantly coupled through tensioning system 708 to the drive component 706a. When the gear and spring tensioning system 708 is assembled with a torsional preload on the springs 716, 720 to apply tension to drive components 706a, 706b, the springs are able to compensate for slack that may develop between the drive components when, for example, the drive systems are decoupled and no torque is applied to the drive inputs. Tensioning systems such as 708 may also maintain tension between drive components (e.g., drive components 608a, 608b of handpiece 604) when unequal motion of the drive components occurs due to friction and axial compliance in drive components 608a, 608b or catheter 602 or due to bending of catheter 602.

In use, for example, when the pitch down drive component 706a is retracted (either through manual or robotic control), the opposing drive component 706b unfurls at least partially as capstan 718 rotates. Via the spring 716, at least some of the torque on the capstan 718 is transferred to gear 710. The torque on gear 710 applies torque to gear 714 in the same direction. The torque on the gear 714 is imparted at least partially, via spring 720 to capstan 722 to prevent any slack from appearing in opposing drive component 706a. Thus, opposing drive components 706a, 706b are maintained in tension. This use of the tensioning system 708 with unequal motions of opposing drive components may be particularly applicable in the instrument system 600 because the unequal motions of the drive components 608a, 608b can find their way past the split lever capstan system of manual actuator 619 to affect cable slack in the inputs.

FIG. 13a schematically illustrates an interventional instrument 750. The instrument 750 includes a catheter system 752 coupled to an instrument handpiece 754. The catheter system 752 houses opposing drive components 756a, 756b for moving the distal end of the flexible body in opposite directions in one degree of freedom (e.g., pitch degree of freedom motion). The instrument 750 has a cable tensioning system 758 which prevents the opposing drive components 756a, 756b from becoming slack and decoupling from the drive inputs or manual actuator.

FIG. 13b illustrates a portion of the tensioning system 758 which includes a capstan 766 coupled to a capstan 768 by a cable 774 fixed to and wound at least partially around the capstans. Capstan 766 is rotatably coupled to a shaft 770 which is rotatably attached to the handpiece 754. A biasing member 762, such as a torsion spring, is supported by the shaft 770 and coupled at one end to the capstan 766 and at another end to a capstan 760. The drive component 756b wraps around the capstan 760. Similarly, capstan 768 is rotatably coupled to a shaft 772 which is rotatably attached to the handpiece 754. A biasing member 764, such as a torsion spring, is coupled at one end to the capstan 768 and at another end to a capstan 762. The drive component 756a wraps around the capstan 762.

Pre-load wind-up of torsion springs 762, 764 maintain tension in drive components 756a, 756b when no torque or lock is applied to the drive inputs or when unequal motions of the drive components would otherwise create slack. In use, for example, when the pitch down drive component 756a is retracted (either through manual or robotic control), the opposing drive component 756b unfurls at least partially as capstan 756 rotates. Via the spring 762, at least some of the torque on the capstan 760 is transferred to capstan 766. The torque on capstan 766 is imparted at least partially, via cable 774 to apply torque to capstan 768. Torque on the capstan 768 is imparted at least partially through spring 764 to apply torque to capstan 762 to prevent any slack created in opposing drive component 756a. Thus, opposing drive components 756a, 756b are maintained in tension.

FIG. 14a schematically illustrates an interventional instrument 800. The instrument 800 includes a flexible body 802 coupled to an instrument handpiece 804. The flexible body 802 houses opposing drive components 806a, 806b for moving the distal end of the flexible body in opposite directions in one degree of freedom (e.g. pitch degree of freedom motion). The instrument 800 has a pulley and spring tensioning system 808 which prevents the opposing drive components 806a, 806b from becoming slack and decoupling from or entangling about the drive inputs or manual actuator.

FIG. 14b illustrates a portion of the tensioning system 808 which includes a pulley 810 fixed to the handpiece 804. A biasing member 812, such as an extension spring, is attached between the drive components 806a, 806b. At least one of the drive components 806a, 806b extends across the pulley 810. In use, the spring 812 is pre-loaded so that if the movements of the drive components 806a, 806b are not equal or if no torque is applied to the inputs, at least some tension in both drive components is maintained. This insures that the drive components do not become disengaged from or entangled about the pulleys or capstans of the tensioning systems or the drive inputs or manual actuator.

In use, for example, when the pitch down drive component 756a is retracted (either through manual or robotic control), the opposing drive component 756b unfurls at least partially as capstan 756 rotates. Via the spring 762, at least some of the torque is applied to the capstan 760 is transmitted to capstan 766. The movement of capstan 766 is imparted at least partially, via cable 774 to rotate capstan 768. Rotation of the capstan 768 is imparted at least partially through spring 764 to rotate capstan 762 to take up any slack created in opposing drive component 756a. Thus, opposing drive components 756a, 756b are maintained in tension.

FIG. 15 illustrates a method of use for an interventional instrument according to an embodiment of the present disclosure. An interventional instrument, such as any of those described in the preceding embodiments, is provided at 852. At 860, with the interventional instrument removed from the drive mechanism, the instrument may be operated in manual mode.

In manual mode, the manual actuator of the interventional instrument receives a force from the user (e.g., the pressure of a user's thumb against a thumb lever) to move the distal end of the elongated flexible instrument. When moved in a first direction (e.g. the thumb lever is toggled toward the distal end of the handpiece), the manual actuator moves a first drive component to control movement of a distal end of the elongated flexible shaft in a first direction (e.g., an upward pitch direction). When moved in a second direction (e.g., the thumb lever is toggled toward the proximal end of the handpiece), the manual actuator moves a second drive component to control movement of the distal end of the elongated flexible shaft in a second direction, opposite the first direction (e.g., a downward pitch direction).

At 856, the interventional instrument is coupled to a robotic surgical system. More specifically, a motorized drive mechanism of a robotic surgical system receives a motor interface of the interventional instrument. Optionally, the motor interface of the interventional instrument is received at the drive mechanism in a direction approximately transverse to the longitudinal axis of the elongated shaft of the interventional instrument to minimize or eliminate motion of the instrument along its axis of insertion into the patient. At 858, the drive input of the motorized mechanism is activated to move the distal end of the elongated flexible shaft in a first degree of freedom (e.g., pitch). In robotic control mode, one of a pair of drive inputs of the interventional instrument receives a force from the motorized drive system to move the distal end of the elongated flexible instrument. When activated, one of the pair of drive inputs moves a first drive component to control movement of a distal end of the elongated flexible shaft in a first direction (e.g., an upward pitch direction). When activated, the other one of the pair of drive inputs moves a second drive component to control movement of the distal end of the elongated flexible shaft in a second direction, opposite the first direction (e.g., a downward pitch direction).

At 860, the motor interface of the interventional instrument is decoupled from the drive mechanism. Optionally, the motor interface of the interventional instrument is decoupled in a direction transverse to the longitudinal axis of the elongated shaft. Coupling and decoupling the instrument from the drive mechanism in a direction transverse to the shaft reduces the risk that the distal end interventional instrument will change insertion depth as the instrument moves between robotic control mode and manual control mode.

Although the systems and methods of this disclosure have been described for use in the connected bronchial passageways of the lung, they are also suited for navigation and treatment of other tissues, via natural or surgically created connected passageways, in any of a variety of anatomical systems including the colon, the intestines, the kidneys, the brain, the heart, the circulatory system, or the like. The methods and embodiments of this disclosure are also suitable for non-interventional applications.

One or more elements in embodiments of the invention may be implemented in software to execute on a processor of a computer system such as control system 116. When implemented in software, the elements of the embodiments of the invention are essentially the code segments to perform the necessary tasks. The program or code segments can be stored in a processor readable storage medium or device that may have been downloaded by way of a computer data signal embodied in a carrier wave over a transmission medium or a communication link. The processor readable storage device may include any medium that can store information including an optical medium, semiconductor medium, and magnetic medium. Processor readable storage device examples include an electronic circuit; a semiconductor device, a semiconductor memory device, a read only memory (ROM), a flash memory, an erasable programmable read only memory (EPROM); a floppy diskette, a CD-ROM, an optical disk, a hard disk, or other storage device, The code segments may be downloaded via computer networks such as the Internet, intranet, etc.

Note that the processes and displays presented may not inherently be related to any particular computer or other apparatus. The required structure for a variety of these systems will appear as elements in the claims. In addition, the embodiments of the invention are not described with reference to any particular programming language. It will be appreciated that a variety of programming languages may be used to implement the teachings of the invention as described herein.

While certain exemplary embodiments of the invention have been described and shown in the accompanying drawings, it is to be understood that such embodiments are merely illustrative of and not restrictive on the broad invention, and that the embodiments of the invention not be limited to the specific constructions and arrangements shown and described, since various other modifications may occur to those ordinarily skilled in the art.

What is claimed is:

1. A system comprising:
    a handpiece body configured to couple to a proximal end of a medical instrument;
    a manual actuator mounted in the handpiece body;
    a plurality of drive inputs mounted in the handpiece body and configured for removable engagement with a motorized drive mechanism;

a first drive component, operably coupled to the manual actuator and operably coupled to one of the plurality of drive inputs, to control movement of a distal end of the medical instrument in a first direction; and a second drive component, operably coupled to the manual actuator and operably coupled to another one of the plurality of drive inputs, to control movement of the distal end of the medical instrument in a second direction.

2. The system of claim 1 wherein the manual actuator includes a first lever and a second lever, wherein the first drive component is operably coupled to the first lever and to one of the plurality of drive inputs to control movement of the distal end of the medical instrument in the first direction and the second drive component is operably coupled to the second lever and to one of the plurality of drive inputs to control movement of the distal end of the medical instrument in the second direction.

3. The system of claim 1 further comprising a tensioning system coupled to the handpiece body and adapted to maintain tension in the first and second drive components.

4. The system of claim 3 wherein the tensioning system includes a pulley system coupled to the first and second drive components.

5. The system of claim 3 wherein the tensioning system includes a gear mechanism interconnecting a pair of the plurality of drive inputs.

6. The system of claim 3 wherein the tensioning system includes a cable interconnecting a pair of the plurality of drive inputs.

7. The system of claim 3 wherein at least one of the plurality of drive inputs includes a capstan coupled to the first drive component and the tensioning system includes a spring coupled to the capstan.

8. The system of claim 3 wherein the plurality of drive inputs includes a pair of opposing drive inputs with each of the opposing drive inputs including a capstan and wherein the pair of opposing drive inputs are connected by a spring.

9. The system of claim 1 wherein the manual actuator includes
   a rack and pinion mechanism housed within the handpiece body and coupled to the first and second drive components and
   a pivotable lever coupled to the rack and pinion mechanism.

10. The system of claim 1 wherein the manual actuator includes
    a capstan housed within the handpiece body and coupled to at least the first drive component and
    a pivotable lever fixedly coupled to the capstan.

11. The system of claim 1 wherein second direction is opposite the first direction.

12. The system of claim 1 further comprising the medical instrument.

13. The system of claim 12 wherein the medical instrument includes an elongated flexible shaft.

14. The system of claim 1 wherein the handpiece body further includes an access port in communication with a lumen of the medical instrument.

15. The system of claim 1 further comprising the motorized drive mechanism which includes a pair of motors adapted to engage a pair of the plurality of drive inputs.

16. The system of claim 1 further comprising a pulley coupled to the handpiece body, wherein the first drive component is bent about the pulley by approximately 90°.

17. The system of claim 1 wherein the handpiece body further includes a bearing surface shaped to receive pressure from a portion of a user hand when the medical instrument is coupled to or decoupled from a robotic manipulator.

18. The system of claim 1 further comprising a latch alignment and release mechanism adapted to releasably couple the plurality of drive inputs to the motorized drive mechanism.

19. The system of claim 1 wherein the plurality of drive inputs are configured to engage the motorized drive mechanism in a direction transverse to a longitudinal axis extending through the medical instrument.

20. The system of claim 1 wherein a proximal portion of an outer sheath of at least one of the drive components is constrained to resist axial movement within the handpiece body.

21. A method of operating a medical instrument, the method comprising:
    providing the medical instrument coupled to a handpiece body, a manual actuator mounted in the handpiece body, a plurality of drive inputs mounted in the handpiece body, and first and second drive components extending within the handpiece body;
    while the plurality of drive inputs are coupled to a motorized drive mechanism, activating one of the plurality of drive inputs to move at least one of the first and second drive components, thereby moving a distal end of the medical instrument in a first degree of freedom; and
    while the plurality of drive inputs are decoupled from the motorized drive mechanism, receiving a user force on the manual actuator to move at least one of the first and second drive components, thereby moving the distal end of the medical instrument in the first degree of freedom.

22. The method of claim 21 further comprising
    providing a tensioning system coupled to the handpiece body; and
    passively maintaining tension in the first and second drive components.

23. The method of claim 22 wherein the tensioning system includes a pulley system coupled to the first and second drive components.

24. The method of claim 22 wherein the tensioning system includes a gear mechanism interconnecting a pair of the drive inputs.

25. The method of claim 22 wherein the tensioning system includes a cable interconnecting a pair of the drive inputs.

26. The method of claim 22 wherein one of the drive inputs includes a capstan coupled to the first drive component and the tensioning system includes a spring coupled to the capstan.

27. The method of claim 21 wherein the manual actuator includes a rack and pinion mechanism housed within the handpiece body and coupled to the first and second drive components and a pivotable lever coupled to the rack and pinion mechanism, the method further comprising moving the distal end of the medical instrument in the first degree of freedom in response to movement of the lever by a user.

28. The method of claim 21 wherein the manual actuator includes a wheel housed within the handpiece body and coupled to the first drive component and a pivotable lever fixedly coupled to the wheel, the method further comprising moving the distal end of the medical instrument in the first degree of freedom in response to movement of the lever by a user.

29. The method of claim 21 further comprising releasing the medical instrument from connection to the handpiece body.

30. The method of claim 21 further comprising receiving a tool through an access port in the handpiece body and into a lumen of the medical instrument.

31. A system comprising:
   a handpiece body configured to couple to a proximal end of a medical instrument;
   a manual actuator mounted in the handpiece body;
   a motorized drive mechanism mounted to the handpiece body;
   a plurality of drive inputs mounted in the handpiece body and configured for removable engagement with the motorized drive mechanism;
   a first drive component, operably coupled to the manual actuator and operably coupled to the motorized drive mechanism, to control movement of a distal end of the medical instrument in a first direction; and
   a second drive component, operably coupled to the manual actuator and operably coupled to the motorized drive mechanism, to control movement of the distal end of the medical instrument in a second direction.

32. The system of claim 31 wherein the manual actuator includes a first lever and a second lever, wherein the first drive component is operably coupled to the first lever to control movement of the distal end of the medical instrument in the first direction and the second drive component is operably coupled to the second lever to control movement of the distal end of the medical instrument in a second direction, opposite the first direction.

33. A method of operating a medical instrument, the method comprising:
   providing the medical instrument coupled to a handpiece body, a manual actuator mounted in the handpiece body, a plurality of drive inputs mounted in the handpiece body, the plurality of drive inputs coupled to a motorized drive mechanism mounted to the handpiece body, and first and second drive components extending within the handpiece body;
   while the motorized drive mechanism is activated, moving at least one of the first and second drive components, thereby moving a distal end of the medical instrument in a first degree of freedom; and
   while the motorized drive mechanism is deactivated, receiving a user force on the manual actuator to move at least one of the first and second drive components, thereby moving the distal end of the medical instrument in the first degree of freedom.

* * * * *